United States Patent [19]
Rakowicz-Szulczynska

[11] Patent Number: 5,939,277
[45] Date of Patent: Aug. 17, 1999

[54] DETECTION AND TREATMENT OF BREAST AND GYNECOLOGICAL CANCER

[76] Inventor: Eva M. Rakowicz-Szulczynska, 7512 Poppleton Plaza, Apt.10, Omaha, Nebr.

[21] Appl. No.: 08/628,687

[22] PCT Filed: Oct. 14, 1994

[86] PCT No.: PCT/US94/11754

§ 371 Date: Jun. 14, 1996

§ 102(e) Date: Jun. 14, 1996

[87] PCT Pub. No.: WO95/10777

PCT Pub. Date: Apr. 20, 1995

Related U.S. Application Data

[63] Continuation-in-part of application No. 08/138,141, Oct. 15, 1993, abandoned.

[51] Int. Cl.$^6$ .................... G01N 33/574; G01N 33/48; C07K 16/00
[52] U.S. Cl. ................... 435/7.23; 436/63; 436/64; 530/388.35
[58] Field of Search ............... 435/7.23; 436/63, 436/64; 530/388.35

[56] References Cited

FOREIGN PATENT DOCUMENTS

0339504 A3  11/1989  European Pat. Off. .......... C07K 7/00
WO 93/07259  4/1993  WIPO .............. C12N 7/00

OTHER PUBLICATIONS

Rakowicz–Szulczynska, E., et al., "Internalization of Anti–gp 120 Monoclonal Antibody and Human Antibodies by HIV–1–Infected T Lymphocytes," *Antibody Immunoconjugates, and Radiopharmaceuticals* 6(4):209–218 (1993).

*Primary Examiner*—Sheela Huff
*Assistant Examiner*—Yvonne Eyler
*Attorney, Agent, or Firm*—Stroock & Stroock & Lavan LLP

[57] ABSTRACT

The present invention provides methods for detecting the presence of HIV-I-crossreactive breast and gynecological cancer-associated antigens in biological samples and to methods for treating these cancers. In a preferred embodiment, these methods utilize a monoclonal antibody developed against a synthetic peptide corresponding to the variable domain of the Human Immunodeficiency Virus (HIV-I) envelope protein gp120 (amino acid regions 308–322). Regions of homology between HIV-I and breast and gynecological cancer sequences are identified as are methods for diagonals and treatment based on the conserved genetic sequences.

10 Claims, 12 Drawing Sheets

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:1:

Arg Ile Gln Arg Gly Pro Gly Arg Ala Phe Val Thr Ile Gly Lys
1             5                  10               15

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

AGCAGCAGGA AGCACTATGG                                                     20

(2) INFORMATION FOR SEQ ID NO:3:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

CCAGACTGTG AGTTGCAACA G                                                   21

(2) INFORMATION FOR SEQ ID NO:4:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

TACATCAGGC CATATCACCT AC                                                  22

(2) INFORMATION FOR SEQ ID NO:5:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

TGAAGGTACT AGTACTTCCT GC                                                  22

(2) INFORMATION FOR SEQ ID NO:6:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:6:

```
CCAGACTGTG AGTTGCAACA G                                              21
```

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:7:

```
CAACAGCCTA CAACC                                                     15
```

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:8:

```
TCTTCTAATC CCAAA                                                     15
```

(2) INFORMATION FOR SEQ ID NO:9:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Gly Arg Ala Phe
1
```

(2) INFORMATION FOR SEQ ID NO:10:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
TCCANTNCAC TAGCTCTACG CCAGNCGNTG NTCAGGCATC TCACGTCTTC TGNGGGCTAG    60

NCTAACAANA TGTTACAGCN TCTANCGCTG TTTGGATTNG AAGAGGTTNT AGGCTGTTGC    120

AACTCACAGC CTGGTAGTAG GTCAG                                          145
```

(2) INFORMATION FOR SEQ ID NO:11:

(i) SEQUENCE CHARACTERISTICS:
        (A) LENGTH: 147 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

TCTTCAACTC NAGAGGACNA CGNNANNCCN AGNTCGGGAT CTCACTGTAC TCTNAGGGTA      60

GCACTTTGCN GGAATGTGCA CAGCNTGGCT ANCGGNGGTA GCAGAGGATG TCGTGCTGAG     120

TGCANCTCAC AGNCTAGGNT NAATATC                                        147

(2) INFORMATION FOR SEQ ID NO:12:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TCCAGAACAG CAGANCTACG NCAGCCCTTG TNAGGAATCT CACNCTACTC GNGAGTAGCC      60

TGNCANAATG TCAATAGACT CTCTCCTGTT NGATTAGAAG AGGNTGTAGG CTGTTGCAAC     120

TCACAGTCTG G                                                         131

(2) INFORMATION FOR SEQ ID NO:13:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GAACAATTTG CTGAGGGCTA TTGAGGCGCA ACAACATCTG TTGCAACTCA CAGTCTGGGC      60

ATCAAGGA                                                              68

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

TGTGACATCA GGCTCAAATC                                                  20

DETECTION AND TREATMENT OF BREAST AND GYNECOLOGICAL CANCER

This application is filed under 35 U.S. C. §371 as a national stage application of the International application PCT/US94/11754, filed Oct. 14, 1994, which is a continuation-in-part of U.S. application Ser. No. 08/138,141, filed Oct. 15, 1993, now abandoned.

DESCRIPTION

1. Technical Field

The present invention relates to newly discovered antigens associated with breast and gynecological cancers and to immunoassay methods for detecting these antigens in biological samples, as well as immunotherapeutic methods for treating these cancers with antibodies that bind to these antigens. More specifically, the invention relates to the discovery of immunological cross-reactivity between antibodies to Human Immunodeficiency Virus (HIV-I) envelope protein gp120 and certain breast and gynecological carcinoma cell surface and chromatin antigens. This cross-reactivity results in the formation of new immunocomplexes which are useful in the immunodiagnostic methods of this invention.

2. Background

Breast carcinoma, together with carcinoma of the ovary, account for one-third of all cancers occurring in women, and together are responsible for approximately one-quarter of cancer-related deaths in females. Cancer of the female genital tract accounts for almost 80,000 cases of invasive cancer each year in the United States, with the majority of these being one of three neoplasms; carcinoma of the cervix, endometrial carcinoma, and celomic epithelial carcinoma of the ovary. Except for cervical cancer, which is definitely linked with Human Papilloma Virus infection, etiological agents involved in malignant transformation of breast, ovarian, or endometrial cells remain unclear. It has been established that susceptibility to breast and ovarian cancer is inherited in some families. Between 5% and 10% of breast cancer and ovarian cancer can be linked with inheritance of a gene conferring high risk, followed by genetic changes in epithelial cells. The gene which is believed to be responsible for inherited breast-ovarian cancer has been localized on the chromosome 17q12-21 and named locus BRCA 1; however, the sequences of the gene located in this locus are completely unknown. Approximately one in 200 women—600,000 women in the United States—have inherited susceptibility to breast cancer which is not only associated with BRCA1, but also with mutations in other genes like P53, Her2/erbB2, estrogen receptor and others. Genetic counseling for families with inherited susceptibility to breast and ovarian cancer and prophylactic mastectomy or oophorectomy represent a widely discussed subject.

Surgery, radiotherapy, and chemotherapy represent three basic methods which are used in management of breast cancer and gynecologic cancer. High mortality of breast cancer and gynecologic cancer. High mortality of breast cancer and hynecologic cancer patients indicates that the currently available diagnostic and therapeutic methods are unsatisfactory.

Immunotherapy and immunodiagnosis with monoclonal antibodies (MAb) represents another approach which has been extensively developing and improving during the past few years. In direct approaches, MAb IgG2a and IgG3 mediate antibody-dependent cellular cytotoxicity and/or exert complement-dependent cytotoxicity. Most frequently used is radio-immunotherapy with radioactively labeled MAb. Immunotoxins, which are the conjugates of MAb with the subunit A of the ricin or diphtheria toxin, exhibit high tumoricidal potential, however have a restricted application due to high cytotoxicity.

Recently, a high number of monoclonal antibodies directed against breast, ovarian, and cervical cancer have been developed and efforts have been undertaken to use those MAbs as immunodiagnostic and immunotherapeutic agents. However, no significant progress has been reported in management of malignancies of the female reproductive tract using these techniques.

A number of HIV-1 peptides and proteins have been identified which elicit neutralizing antibodies in animals. EP-A-33504 describes chemically synthesized amino acid peptides having the sequence of amino acids from the HIV-1 virus which may be used to induce the production of HIV inhibiting antibodies for the treatment of AIDS and AIDS-related complex. However, the prior art has not disclosed a a means of synthesizing and using monoclonal antibodies for purposes of detecting and treating breast and gynecological cancer.

It is an object of this invention to provide immunodiagnostic and immunotherapeutic methods which are believed to be an innovative approach to managing breast and gynecological cancers.

SUMMARY OF THE INVENTION

Briefly stated, the present invention provides methods for detecting the presence of HIV-1-crossreactive breast and gynecological cancer-associated antigens (as hereinafter defined) in biological samples and to methods for treating these cancers. In a preferred embodiment, these methods utilize a monoclonal antibody developed against a synthetic peptide corresponding to the variable domain of the Human Immunodeficiency Virus (HIV-1) envelope protein gp120 (amino acid region 308–322), herein referred to as MAb 5023. This MAb can be purchased from DuPont/NEN, 549 Albany Street, Boston Mass. 02118, and is listed in the catalog of this company entitled "DuPont/NEN Research Products 1992–1993" under Catalog Number, NEA-9305, the Product description of which is "HIV Monoclonal Antibody gp120-Neutralizing (sequence specific) (mouse) 0.5 mL". In accordance with this invention, MAb 5023 has been found to be unique in its ability to penetrate the cell and localize within the cell nucleus and in its ability to recognize a family of antigens expressed by breast cancer and hynecological cancers.

Consequently, in accordance with this invention there is provided a method for diagnosis of breast cancer and hynecological cancer comprising exposing a biological sample from a host suspected of having said cancer to MAb 5023 and detecting the presence of HIV-crossreactive immunocomplexes. Fortuitously, this invention makes possible a simple and direct in vivo diagnosis of cervical cancer by administration of MAb 5023 to the cervix and then detecting the presence of immunocomplexes formed between said antibody and cell surface proteins p120 and p41 is another embodiment.

In one aspect of the invention, the method comprises detecting HIV-I-crossreactive breast carcinoma-associated antigens in a biological sample comprising (a) exposing a biological sample, suspected of containing the antigens, to an antibody which recognizes the following cell membrane proteins: p160, p80, p45, and p24 and the following chromatin protein: p24, and (b) detecting the presence of immunocomplxes formed between said antibody and said proteins.

Related, is a method for detecting HIV-I-crossreactive, gynecological cancer-associated antigens in a biological sample comprising (a) exposing a biological sample, suspected of containing the antigens, to an antibody which recognizes the following cell membrane proteins, p120, p41, and p24 and the chromatin protein, p24, and (b) detecting the presence of immunocomplexes formed between said antibody and said proteins.

The immunocomplexes thus formed constitute and embodiment of this invention and comprise (a) at least one of the following cell membrane proteins, p160, p80, p45, or p24, or the chromatic protein, p24, and (b) an antibody which recognizes each of said proteins. In a preferred embodiment the antibody is MAb 5023. Generally the immunocomplexes of this invention are in an immobilized form. In this form the immunocomplexes are insolubilized, or otherwise supported, on a variety of standard immobilization substrates. Examples of materials to which the capturing agents can be attached are glass, synthetic polymers, synthetic resins, cellulose, nitrocellulose, and various metals. Procedures for attaching these capturing agents will vary depending upon the agent and substrate employed, but, in general, are well known in the art. Some of the methods for binding of antibodies to a solid matrix are discussed in E Harlow and D Lane, *Antibodies: A Laboratory Manual*, New York: Cold Spring Harbor Laboratory, pp. 511–552, 1988.

Another aspect of the present invention is a method for treating breast cancer and gynecological cancer, selected from the group consisting of ovarian, cervical, endometrial, and vulvar cancer, comprising administering to a patient an antibody which translocates and internalizes to the nucleus of the cell and which forms immunocomplexes with the HIV crossreactive antigens of this invention, e.g., MAb 5023. The antibody can be administered alone or conjugated with a radioactive or cytotoxic ligand, and is administered in a pharmaceutically effective dosage form, generally, for intravenous or intraperitoneal injection.

The HIV-I-crossreactive cancer-associated antigens of this invention are the p160, p80, p45, and p24 cell membrane proteins and the p24 chromatin protein for breast cancer, and p120, p41, and p24 cell membrane proteins and the p24 chromatin protein for gynecological cancers (i.e., ovarian, cervical, endometrial, and vulvar cancer).

In all of the methods briefly described above, the antibody may be labeled with an enzyme, fluorochrome, radioisotope, or luminescer. In such cases the step for detection would normally be by enzyme reaction, fluorescence, radioactivity, or luminescence emissions, respectively.

The methods described above may be applied to a variety of biological samples in order to detect the presence of the HIV-I-crossreactive cancer-associated antigens of this invention or antibodies thereto. Bodily secretions, bodily fluids, and tissue specimens are all suitable samples in this regard. Examples of bodily secretions include cervical secretions, vaginal secretions, human breast milk, urine, and intraperitoneal ascitic fluid. Suitable bodily fluids include blood. Examples of tissue specimens include a variety of biopsies, such as a biopsy of cervical dysplasia, cervical cancer, ovarian cancer, vulvar cancer, lymph nodes, and bone marrow. In addition tissue from all areas may be examined in connection with a post mortem examination, including primary tumors and metastatic tumors, lymph nodes, bone marrow and all organs.

In accordance with the present invention, continuous hybrid cell lines can be established that produce monoclonal antibodies directed against an antigenic determinant of the HIV-I-crossreactive cancer-associated antigens of this invention for use in the methods described above. In a particularly preferred embodiment, the cell line comprises the hybridoma clone for MAb 5023.

Figure 1A:
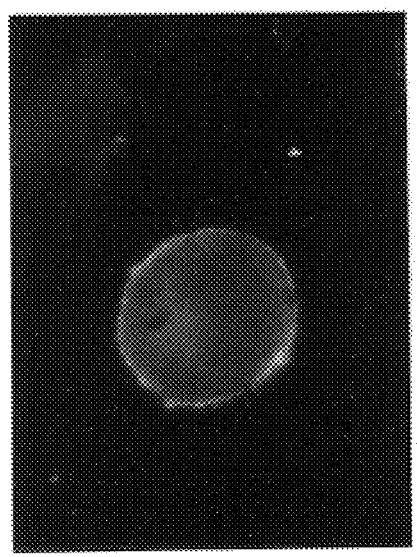
FIGS. 1A–1E. Immunofluoroescence staining of SKBr 5 (A–D) and MCF7 (E) breast carcinoma cells with fluorescein-conjugated sheep anti-mouse IgG after incubation with MAb 5023 at 0° C. for 15 min (A), or at 37° C. for 1 h (B), 3 h (C), and 24 h (D, E).
Figure 1B:
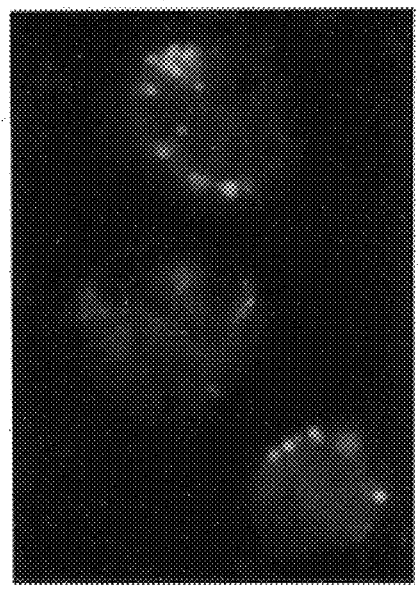

Proteins were separated in 10% polyacrylamide gel with 0.1% sodium dodecyl sulfate (SDS) in 250 mM Tris-HCl (pH 8.3), 195 mM glycine, and 0.1% SDS, according to Laemmli et al (76). Each lane corresponds to 3×10$^5$, except lane 7 which corresponds to 5×10$^4$ cells. Blotting of proteins from the polyacrylamide gel to the PVDF membrane was performed in 25 mM Tris-HCl (pH 8.6), 192 mM glycine buffer, containing 10% methanol. Filters were incubated with 1% BSA for 16 h, at 0° C., then with MAb anti-HIV-I gp120 (DuPont) (5 μg/ml), washed with Tris-glycine buffer, and incubated with alkaline phosphatase-conjugated goat anti-mouse IgG for 1 h. After washing with TBST, membranes were incubated with 0.1% 1-naphthyl-phosphate and Fast Red, in 100 mM Tris-HCl pH 9.5, 100 mM NaCl, 5 mM MgCl$_2$). A: MCF7 breast carcinoma (lanes 1,2), SiHa cervical carcinoma (lanes 3,4), endometrial cancer (lanes 5,6) and cervical cancer (lane 7) proteins. B: ovarian cancer (lane 1) and normal ovarian tissue (lane 2). C: normal skin, muscle and cervical tissue and normal vaginal mucosal proteins.

Figure 10:
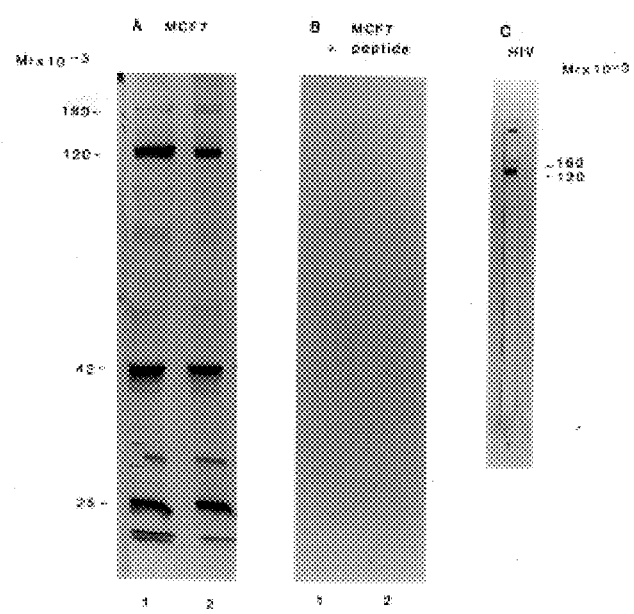

FIG. 10 Competitive inhibition of MAb anti HIV-I gp120 binding to the cytoplasmic proteins extracted from mixed Mullerian tumor (A) by peptide RIQRGPGRAFVTIGK SEQ ID NO:1 (B), against which the MAb was developed. The same amount of proteins were separated in A and B, lane 1 (equivalent of 10$^6$ cells) and in A and B, lane 2 (equivalent of 0.5×10$^6$) (Peptide (18 μg/ml) was incubated with MAb anti-HIV-I gp120 (5μg/ml) for 1 hr on ice, next it was incubated with the filter (B). In control (A), the filter was incubated with MAb alone).

Reactivity of MAb anti HIV-I gp120 with PVDF strip containing HIV proteins extracted from AIDS patients' blood (DuPont) (C). Cytoplasmic, chromatin and total proteins were obtained as described in (Cells or sections of cancer or normal tissues, obtained during standard surgical procedures, were homogenized in 0.35 M sucrose/10 mM KCl/1.5 mM MgCl$_2$/10 mM Tris-HCl (pH 7.6)/0.12% Triton X-100/12 mM 2-mercaptoethanol (1 ml/3×10$^6$ cells or 0.25–1 ml/cm$^3$ tissue), and centrifuged at 600×g for 10 minutes. Supernatant was the crude, membrane-containing cytoplasmic fraction. The nuclear pellet was first washed with 0.2 M sucrose/3 mM CaCl$_2$/50 mM Tris-HCl (pH 7.6), and then with 0.14 M NaCl/10 mM Tris-HCl (pH 8.3) and centrifuged at 700×g for 10 minutes. The pellet was swollen in 1 mM Tris-HCl (pH 7.9) and centrifuged throughout the 1.7 M$^-$ sucrose 10 mM Tris HCl (pH 7) at 160,000×g for 80 minutes. Chromatin was pelleted at the bottom of the tube.

Proteins were separated in 10% polyacrylamide gel with 0.1% sodium dodecyl sulfate (SDS) in 250 mM Tris-HCl (pH 8.3), 195 mM glycine, and 0.1% SDS, according to Laemmli et al (76). Each lane corresponds to 3×10$^5$, except lane 7 which corresponds to 5×10$^4$ cells. Blotting of proteins from the polyacrylamide gel to the PVDF membrane was performed in 25 mM Tris-HCl (pH 8.6), 192 mM glycine buffer, containing 10% methanol. Filters were incubated with 1% BSA for 16 h, at 0° C., then with MAb anti-HIV-I gp120 (DuPont) (5μg/ml), washed with Tris-glycine buffer, and incubated with alkaline phosphatase-conjugated goat anti-mouse IgG for 1 h. After washing with TBST, membranes were incubated with 0.1% 1-naphthyl-phosphate and Fast Red, in 100 mM Tris-HCl pH 9.5, 100 mM NaCl, 5 mM MgCl$_2$).

Figures 11A, 11B, 12:
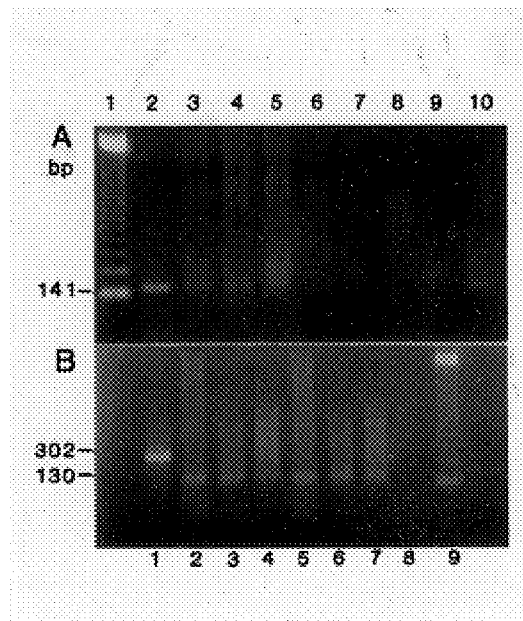

FIGS. 11A and 11B. Representative DNA amplification analysis with primers SK 68/SK 69 (A) and with P1/P2 (B) primers (Polymerase chain reaction (PCR) occurred in the solution containing: 10 mM KCl, 10 mM (NH$_4$)SO$_4$, 200 mM Tris-HCl, 20 mM MgSO$_4$, 1% Triton X-100 dNTP (10 mM each of dATP, dTTP, dCTP, and dGTP), 120–250 ng of the primer, 2.5U Taq polymerase, water up to 30 μl. DNA template was added to the amount of 0.2–1 μg (20 μl), and paraffin oil (70–100 μl). The reaction occurred in a thermal cylinder (30–40 cycles). PCR products were separated in 1% agarose gel with ethidium bromide).

A) lane 1: 123 bp marker, lane 2: HIV-I infected T-cells, 3: SiHa, 4: MCF7, 5: mixed Mullerian tumor, 6–8: normal skin (different patients), 9: no template, 10: endometrial cancer B) lane 1: HIV-I infected T-cells, 2–3: SiHa (1 μg and 0.1 μg, respectively), 4: mixed Mullerian tumor, 5–6: MCF7 (1μ and 0.1 μg, respectively), 7: endometrial cancer, 8: normal skin, 9: 123 bp marker.

FIG. 12. Sequences of 140–150 bp DNA fragments of cervical cancer SiHA (SEQ ID NO:10) endometrial cancer obtained during standard surgery (EIV) (SEQ ID NO:11) and breast cancer MCF7 (SEQ ID NO:12) amplified by PCR with primers SK 68/SK 69 (see FIG. 3A). Nucleotides identical in at least two or more cell types are boxed. 21 bp of the region identical or with high homology to HIV-I are marked with stars.

FIGS. 13A–13G. Transmission electron micrograph of viral particles in SiHa (A,C) and MCF7 (B,C) cells and of extracellular vesicle obtained from MCF7 cells (D). Viral particles negatively stained with urgnyl acetate (E). In A, D and E, samples were immuno-gold labeled with MAb anti-HIV-I gp120. The sizes of the immuno-gold particles were 15 mm (A,D) and 10 nm (E). V–viral particles.

Figure 14A:
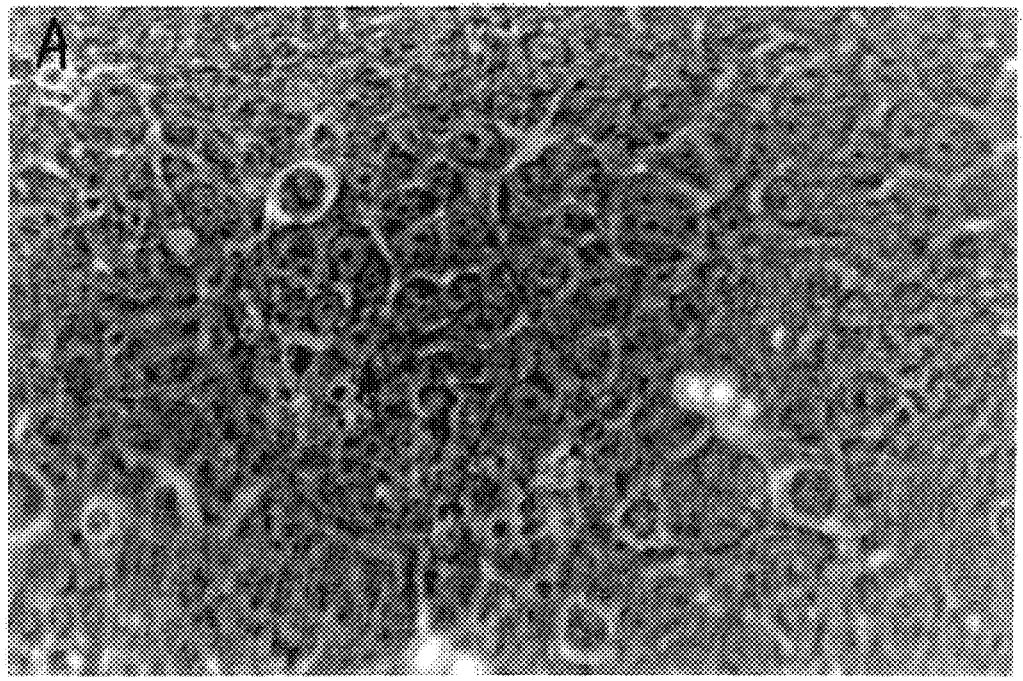
Figure 14B:
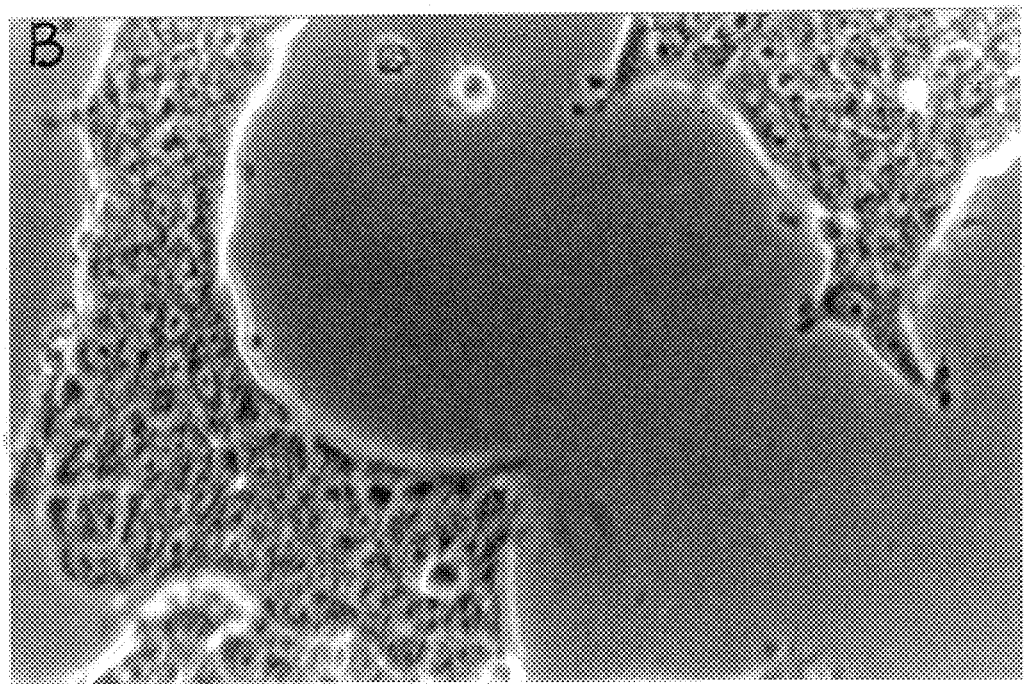

FIGS. 14A and 14B. Effect of antisense oligonucleotide RAK-I on growth of breast cancer MCF7 cell line. Cells were grown for 4 days in the absence (A) or presence (B) of the antisense oligonucleotide RAK-I (5'-CCAGACTGTGAGTTGCAACAG-3') SEQ ID NO:6 added daily at the concentration of 100 μg/ml (day 1) and 50 μg/ml (days 2 and 3). Oligonucleotide 5'-TGTGACATCAGGCTCAAATC-3'(SEQ ID NO:14) was used as a negative control and did not affect cell growth (not shown).

DETAILED DESCRIPTION OF THE INVENTION

MAb 5023, developed against amino acid residues 308–322 of the variable V3 loop of HIV-I, reacted in Western blotting with a 160,000 M$_2$ (p160) and 80,000 M$_2$ (p80) cell surface antigens. Protein p160 seems to represent an oligomeric form of p80. Another MAb, 5025, directed against the same region 308–322, and MAb against amino acid regions 307–328 and 308–332, did not recognize p160 or p80. Although MAb 5023 and MAb 5025 were developed against the same synthetic peptide, there are minor differences in the structure of the core epitope recognized by these MAb, which account for the several-fold higher affinity of MAb 5023 than that of MAb 5025. All of the MAb tested recognized another cell membrane antigen, p45. It is not established whether p45 represents an independent protein, a degradation, or a processing product of p160. Since MAb 5023 was the only MAb which was able to enter breast carcinoma cells and translocate to the nucleus, it is likely that p160 and (p80) express a specific epitope which is critical for MAb internatlization. An unspecific adsorption of the cell membrane-bound $^{125}$I-MAb 5023 to the chromatin during cell fractionation may be eliminated, since p160, p80, and p45 represent the specific markers of the cell membrane fraction and are not found in the chromatin. The fact that MAb 5023, but none of the other MAb, was internalized suggests that an antibody binding to a cell surface antigen is not sufficient to induce the process of internalization. Instead, a specific epitope of the cell surface antigen must be involved. The latest observation is consistent with previous studies, which proved that only a few from many MAb developed against tumor-associated antigens are internalized, while others are unable to enter the cell.

Four antigens, p160/p80, p45, and p24 have been detected in breast cancer, and three antigens, p120, p41, and p24 are commonly expressed by cervical, ovarian, endometrial, and vulvar cancer. All antigens, except for p24 are selectively expressed in the cytoplasmic/plasmamembrane fraction. Protein p24 was detected in both plasmamembrane and chromatin fractions.

Proteins p160/p80, p45, p120, and p41 were undetectable in melanoma, colorectal carcinoma, normal breast epithelial cells and, in non-infected lymphocytes. The low molecular weight protein p24 is expressed in epithelial cells, lymphocytes, and several cancer types.

Internalization of MAb 5023 was also detected in cervical cancer cells which express p120. The epitope recognized by MAb 5023, which may be involved in internatlization, is well characterized. The MAb 5023 was developed against amino acid sequences 308–322 (RIQRGPGRAFVTIGK) (SEQ ID NO:1) of the variable loop of HIV-I gp120, but this MAb binds to the epitope GRAF (SEQ ID NO:9). G preceding RAF is believed to be critical for internatlization.

Only MAb 5023, but none of other MAbs against HIV crossreact with cancer antigens which suggests that p160 and p120 are the proteins which mediate internalization. Lack of reactivity of p160 and p120 with other MAbs directed against loop V3 of HIV-I gp120 suggests that holology of cancer antigens and HIV antigen may be accidental and restricted to a very short amio acid region. On the other hand, the same molecular weights of gynecological cancer and HIV antigens (Mr 120,000), and correlation of the molecular weight of the breast cancer antigen with the percursor for HIV gp120 (Mr 160,000) suggests that cancer proteins may represent products of a retrovirus of homology to HIV. This speculation is supported by homology of the other cancer antigens (p45/41, p24) to HIV antigens. Few other MAbs against the variable region of HIV gp120 also recognized p45 on the cell membrane. Moreover, antibodies from AIDS-patients which have been affinity-purified using HIV-I gp120, recognized p80 and p45 in breast cancer cells); p41 in ovarian cancer.

MAb 5023, when internalized and translocated to the nucleus, stimulated RNA synthesis and promoted growth of breast cancer cells. In contrast, growth of cervical cancer cells was by 30–50% inhibited by MAb 5023.

Stimulatory effect of MAb 5023 on growth of breast cancer cells, and inhibitory effect on growth of cervical cancer cells suggests that p160 and p120 expressed by cancer cells may represent a growth factor receptor-like product(s) of a cellular proto-oncogene. Retroviral origin of HIV-crossreactive antigens is also a possibility.

In addition to the potentially diagnostic and prognostic value of HIV-crossreactive cancer antigens, an ability to internalize MAb 5023 makes these antigens excellent targets for immunotherapy. Specificity of MAb 5023 interaction with breast cancer and gynecological cancer as well as internalization and chromatin binding, make MAb 5023 a potentially useful vehicle for different drugs destined to the cytoplasm and/or nucleus. In accordance with this invention, MAb 5023 is also used as a vehicle for the radioactive ligand ($^{125}$I) and for the antisense oligonucleotide complementary to proto-oncogene Neu/HER-2, also called erbB-2. Neu-oncogene encodes cell surface receptor p185Neu which exhibits strong structural homology to BGF receptor. The oncogenic potential of Neu is released by multiple genetic mechanisms, including point mutation within the transmembrane region, truncations of noncatalytic sequences at both the cytoplasmic and the extracellular domains or by amplification. Particularly, a strong association between Neu amplification and overexpression and clinical outcome has been reported in breast and ovarian cancer. It was shown that MAbs directed against the product of the oncogene Neu inhibit growth of cancer. Down regulation of the cell surface receptor Neu expression by antisense oligonucleotides will significantly inhibit growth of breast cancer and ovarian cancer. Since MAb 5023 is efficiently internalized, another embodiment of this invention is antisense therapy, in which an oligonucleotide complementary to specific regions of the protooncogene Neu is conjugated with MAb 5023.

Antisense research has been expanded during the last five years. Antisense is the term coined to describe the interaction between oligonucleotides complementary to sense (pre-mRNA or mRNA) molecules that inhibit the production of the protein product. It has been broadened to describe any therapeutic oligonucleotide interaction with nucleic acids. The mechanisms which are involved in antisense oligonucleotides action involve: inhibition of translation through the blocking protein binding to specific regions of mRNA, formation of the triplex between double stranded mRNA and the antisense which is degraded by the RNase H, transcriptional arrests after binding of the oligonucleotide to DNA which prevents initiation or elongation of transcription, inhibition of splicing, disruption of necessary RNA structure, destabilization, inhibition of polyadenylation and others. Few major problem uncovered in the application of the antisense concept are: 1) extracellular degradation of the antisense oligonucleotide by nucleases present in the blood, skin and other tissues at the site of administration 2) uptake by the cells through endocytosis and release into the appropriate cellular compartment 3) kinetics of hybridization with nucleic acids and affinity to the garget nucleic acid. Chemical modifications at the 3' and 5' ends of the oligonucleotides were developed to decrease degradation of anti-sense oligonucleotides. Two approaches have been tested in order to increase antisense oligonucleotide delivery to the cell: liposome mediated uptake and membrane-receptor-mediated transport systems. Cholesterol, poly(L-lysine), interleukin, 1,2-di-O-hexadecyl-rac-glycero-3-H-phosphate conjugated oligonucleotides have been synthesized for the purpose of utilizing specific protein-mediated endocytic pathways. Uptake of the oligonucleotides conjugated with the specific ligand was significantly higher. Mechanism of release of oligonucleotides from endosomal vesicles is not clear and it is speculated that it may be induced by conformational changes of endosomal membranes, transient membrane destabilization or other mechanisms.

Another embodiment of this invention is the application of a MAb which is able to internalize and localize into the cell nucleus, e.g., MAb 5023, to deliver an antisense oligonucleotide to the target cells (e.g., anti-Neu and other targets). Compared to other delivery systems, use of MAb which specifically interacts with breast cancer and gynecological cancer cells provides a new opportunity to target antisense oligonucleotide into a specific locus. In addition, since MAb is found inside the cell in a nondegraded form, and it passes the endocytic membrane very efficiently, immuno-antisense therapy may represent an approach to more general methods of genetic therapy.

In producing monoclonal antibodies in accordance with the present invention, continuous hybridoma cell lines are established which synthesize and secrete monoclonal antibodies which bind to the HIV-I-crossreactive cancer-associated antigens of this invention. In the preferred embodiment, the MAb is specific for a peptide corresponding to the variable domain of the Human Immunodeficiency Virus (HIV-I) envelope protein gp120 (amino acid region 308–322).

As a first step in the production of such monoclonal antibodies, animal hosts are immunized according to a conventional protocol in order to induce the development of specifically immune lymphocytes (known as plasma cells) which produce antibodies to the antigen. These lymphocytes are recovered from the spleen of the immunized host and are fused according to conventional experimental protocols with myeloma tumor cells derived from the same animal species to form giant somatic cell hybrids. These hybrid fusion protocols, originally reported by G Kohler and C Milstein (*Nature* 256: 495–497, 1975) are generally known by those skilled in the art.

The cell-cell hybrids exhibit characteristics of both parent cell types used in the fusion: like the malignant myeloma parent, fused cell hybrids have the capacity to grow rapidly and indefinitely in tissue culture; in addition, they have the capacity to secrete large amounts of the antibody specified by the genes of the normal antibody-secreting lymphocyte parent that participated in the fusion. These hybrid cell lines are called "hybridomas." After appropriate selection and cloning, they are propagated in tissue culture or in a genetically identical or immunocompromised animal for an indefinite period in order to continuously produce antibody to the antigen.

In order that they be easily detectable in certain assays, the antibodies of the present invention can be labeled with any of a variety of standard substances which include radioactive, fluorescence, or enzyme markers. Examples of such standard markers are:

1. Radioactive: tritium, carbon-14, phosphorus 32, iodine-125;
2. Fluorescent: fluorescein, rhodamine, phycoerythrin, Texas red;
3. Enzyme: Horseradish peroxidase, alkaline phosphatase, B-galactosidase.

Methods for labeling antibodies with these markers, and for detecting such markers, are generally well known in the art, e.g., see Golub and Geen, "Immunology: A Synthesis", Second Edition, Sinauer Associates, Inc., Sunderland, Mass. (1991), pages 167–175.

MATERIALS AND METHODS

Cell Lines

SKBr5, SKBr3, MCF7, BT12, and CAMA breast carcinoma cell lines, SW1116 and SW707 colorectal carcinoma cell lines, melanoma 451 LU (The Wistar Institute), and the T-cell lymphoma cell line SUPT1 were grown in Eagle's minimal essential medium/Leibovitz's L15(3:4) medium supplemented with 10% fetal bovine serum. Cell line SiHa (cervical cancer) was obtained from the American tissue Culture Collection.

Human Cancer: Gynecological cancer (cervical, ovarian, vulvar, and endometrial) was obtained during normal surgical procedures (University of Nebraska Medical Center).

MAb and Human Antibodies

MAb 5023 and MAb 5025 (against HIV-I gp120 amino acid regions 308–322) are from the DuPont Company, (See AIDS Res and Human Retroviruses 1990; 6:1115–1123.) MAb 0.5b against the region was obtained from Dr. S. Matsushita of the Kumamoto University Medical School in Japan. (See AIDS Res and Human Retroviruses 1988; 4:187–197.) VM77 (307–328) was obtained from Dr. F. Veronese of Bionetics Research, Inc. Human antibodies to env-2-3were provided by Dr. K. S. Stimer, Chiron Research Laboratories, Emeryville, Calif. Antibodies to env-2-3 represent a fraction of pooled sera from humans identified and confirmed to be seropositive in HIV-I serological assays, obtained by purification on the affinity column containing an unglycosylated form of HIV-I envelope protein gp120 which was produced in genetically engineered yeast. (See *Vaccines* 1990. Cold Spring Harbor Labs, Cold Spring Harbor, N.Y., 1990, pp 313–320; and *Science* 1991; 254:105–108.) Iodination of MAb was routinely performed by the IODOGEN method. (See *Arch Biochem Biophys* 1989; 271:366–379.) Specific activity of MAb was 10–20 cpm/pg, and of human antibodies, 3–6 cpm/pg IgG.

Intracellular Localization of MAb in Intact Cells Shown by Indirect Immunofluorescence Staining Cells grown as monolayers were replated at a density of $5 \times 10^5$ ml in Nunc slide flasks (Denmark). After 24 h, the tested MAb were added at concentrations from 10–100 ng/ml. After 30 min or after 1 h, cells were washed 3 times with phosphate-buffered saline, fixed with 50 and 100% ethanol (10 min each), washed 3 times with PBS, and incubated 1 h at 37° C. with fluoresceine-conjugated sheep anti-mouse IgG serum (Collaborative Research). After washing 3 times with PBS, cells were examined in a fluorescence microscope.

Intracellular Localization of $^{125}$I-MAb or $^{125}$I-Antibodies

Cells grown as confluent monolayers were seeded in a fresh medium at a density of $10^5$ cells/per cm$^2$ in a Nunclone (Denmark) flask. After 24 h, $^{125}$I-labeled mouse MAb or $^{125}$I-labeled human IgG was added at a concentration of 100–300 ng/ml and cells ($10$–$20 \times 10^6$) were labeled for 24 h. Cell fractions were obtained as described in *Arch Biochem Biophys*, 1989; 271:366–379.

Cells were washed 3 to 5 times with PBS, homogenized in 0.35 M sucrose/10 mM KCl/1.5 mM MgCl$_2$/10 mM Tris-HCl (pH 7.6)/0.12% Triton X-100/12 mM 2-mercaptoethanol, and centrifuged at 600 g for 10 min. The supernatant, defined as the cytoplasmic fraction (crude), was centrifuged for another 30 min at 10,000 g to remove mitochondria, and then for 1 h at 100,000 g to obtain the microsomal (plasma membrane) fraction. The nuclear pellet was first washed with 0.2 M sucrose/3 mM CaCl$_2$/50 mM Tris-HCl (pH 7.6) and then with 0.14 M NaCl/10 mM Tris-HCl (pH 8.3) and centrifuged at 700 g for 10 min. Nucleoplasmic proteins extracted with 0.14 M NaCl were defined as the "sap protein" fraction. The pellet was swollen in a small amount of 1 mM tris-HCl (pH 7.9) and centrifuged throughout the 1.7 M sucrose, 10 mM Tris-HCl (pH 7), at 160,000 g for 80 min. Chromatin was pelleted at the bottom of the tube, and nuclear membranes were taken at the interface. Nucleoplasm (the residual fraction after extraction with 0.14 M NaCl) was recovered from the top, and mixed with the "sap protein" fraction. Radioactivity of $^{125}$I-MAb bound to the particular cell fractions was calculated using Avogadro's number and specific activity of the $^{125}$I-MAb.

Incubation of Nuclei with $^{125}$I-MAb

Intact nuclei were isolated by homogenization in 0.25 M sucrose, 10 mM KCl, 1.5 mM MgCl$_2$, 10 mM Tris-HCl (pH 7.6), 12 mM 2-mercaptoethanol, 0.02% Triton X-100, centrifugation at 600 g for 10 min, and purification through 2.2 M sucrose, 10 mM Tris-HCl (pH 7.9), 1.5 mM $MgCl_2$ (90,000 g for 60 min).

Nuclei ($2-3\times10^6$) were incubated with $^{125}$I-MAb (10 ng/ml) in an incubation medium containing 0.25 M sucrose, 20 mM Tris-HCl (pH 7.8) 10 mM $MgCl_2$, and 500 ng/ml unlabeled bovine serum albumin. After incubation, nuclei were centrifuged (600 g for 10 min), washed 3 times with 50 mM Tris-HCl (Ph 7.5), 12.5 mM NaCl, 12.5 mM $MgCl_2$, homogenized in 1 mM Tris-HCl (pH 7.6), and centrifuged through 1.7 M sucrose and 10 mM Tris-HCl (pH 7.9). Nucleoplasm was taken from the top, nuclear membranes from the interface ,and chromatin from the bottom of the tube. Radioactivity of $^{125}$I-MAb in the indicated nuclear fractions was measured and the number of $^{125}$I-MAb molecules was calculated as described (Narod S A, et al. *Lancet*, 338, 82–83, 1991). Specificity of $^{125}$I-MAb uptake was estimated by comparing the nonspecific adsorption level of $^{125}$I-BSA or $^{125}$I-non-internalized MAb (Narod S A, et al. *Lancet*, 338, 82–83, 1991).

The inhibitory effect of wheat germ agglutinin (WGA), which binds N-acetylglucosamine of the nuclear pore protein and blocks intracellular uptake of proteins (11, 12), was tested by incubating the isolated nuclei with $^{125}$I-MAb in the presence of increasing concentrations of WGA (0.625–2.5 mg/ml).

Electrophoresis of Proteins

Chromatin and membrane proteins were analyzed by electrophoresis in 7.5–15% polyacrylamide gel with 0.1% sodium dodecyl sulfate (SDS) in buffer containing 250 mM Tris-HCl (pH 8.3), 195 mM glycine, and 0.1% SDS, according to Laemmli et al. (*Nature* 1971;227;680–685.) Gels were run at 100 V for 4 h, stained with Coomassie blue, dried, and autoradiographed. In an alternative approach, $^{125}$I-anti-human IgG was replaced by alkaline phosphatase-conjugated anti-mouse IgG.

Western Blotting

Blotting of proteins from the polyacrylamide gel to the nitrocellulose or a PVDF membrane was performed in the TBST buffer containing 10 mM Tris-HCl (pH 8), 150 mM NaCl, and 0.05% Tween 20.

Transfer is performed at 50 V overnight. Membranes were washed with water, followed by TBST buffer. Filters were incubated with 1% BSA in TBST for 16 h, at 0° C., then incubated with a mouse MAb or human anti-HIV-I antibody for 1 h (2 mg/ml), washed with TBST, and incubated with $^{125}$I-sheep anti-mouse IgG or $^{125}$I-labeled anti-human IgG (1 mCi) for 1 hr. After an extensive washing, the filter was dried and autoradiographed. In some instances, $^{125}$I-anti-human IgG was replaced with alkaline phosphatase/conjugate anti-mouse IgG.

Immunoprecipitation of the Cell Membrane Proteins Recognized by Monoclonal Antibody MAb 5023

SKBr5 cells were incubated for 18 h with [$^{35}$S]methionine (10 mCi/ml, specific activity 1000 Ci/mmol) and fractionated into cytoplasm, nucleoplasm, nuclear membranes, and the chromatin described above. Cytoplasm was centrifuged (105,000 g, 1 h), and a pellet containing microsomal fraction was dissolved in 10 mM Tris (pH 7.4), 0.5% Nonidet NP40, 0.14 M NaCl, 5 mM BDTA, and 1 mM phenylmethylsulfonyl fluoride. The solubilized microsomal fraction containing cytoplasmic membranes was incubated with MAb 5023 against the HIV-I gp120 (2–5 mg/membranes from $5\times10^5$ cells) for 1 h at 4° C. with formalin-fixed *Staphyloccus aureus* (Calbiochem). After incubation, *S. aureus* containing the MAb-cell surface protein complexes was washed with 10 mM Tris-HCl (pH 7.4), 0.5% Nonidet NP40, 0.1% SDS, and 0.14 M NaCl. Immunoprecipitated proteins were analyzed electrophoretically according to Laemmli (*Nature* 1971;227:680–685).

Effect of MAb 5023 on RNA Synthesis and Cell Proliferation

SKBr5 cells were incubated 1 or 24 hr in the cell culture media containing [5,6 3H]uridine (Amersham, sp act 48 Ci/mmol) and 0 or 100 ng/ml of MAb 5023. After the incubation, cells were fractionated into the cytoplasm, nucleoplasm, nuclear membranes and chromatin as described above. Radioactivity of chromatin-bound RNA, nucleoplasmic RNA, and cytoplasmic RNA was tested in the fraction precipitated with 10% trichloroacetic acid and filtered on Whatman GF/C filters.

Effect of MAb 5023 on cell proliferation was tested by counting the cells after 4 days of the exposure to 0 or 100 ng/ml of MAb 5023.

RESULTS

Immunofluorescence Detection of MAb 5023 Inside the Breast Carcinoma Cells

Breast carcinoma SKBr5, MCF7, and colorectal carcinoma SW1116 cells were incubated for different periods with five MAb directed against the V3 loop of HIV-I gp120, followed by incubation with fluoresceine-labeled sheep anti-mouse IgG (FIG. 1).

After 15 min of SXBr5 cell incubation with MAb 5023 at 0° C., an imunofluorescence ring surrounded breast carcinoma cells, which means that MAb 5023 bound to the cell surface receptor (FIG. 1A). After 15 min to 1 h of incubation at 37° C., fluorescent spots were detected inside the cytoplasm (FIG. 1B), which suggests that the MAb was internalized and localized in the endosomal vesicles.

Figure 1C:
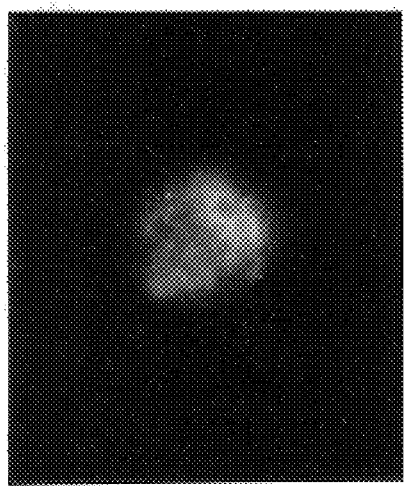
Figure 1D:
Figure 1E:
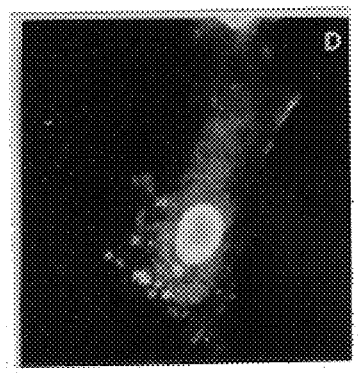

After longer exposure (3–5 h), the fluorescence of cytoplasm became more diffuse and seemed to be distributed within the cytoplasm and the nucleus (FIG. 1C). After 24 h of incubation of breast carcinoma cells, the strong fluorescence of the nucleus was easily distinguishable from the much weaker fluorescence of the cytoplasm (FIG. 1D). The predominantly nuclear location of MAb 5023 was also observed in NCF7 cells (FIG. 1E). MAb 5023, after 24 h of incubation, was undetectable in control colorectal carcinoma cells (not shown). MAb 5025, 0.5b, and VM77 were undetectable in breast carcinoma cells (not shown).

Internalization of $^{125}$I-MAb Against HIV-I gp120 by Breast Carcinoma Cells Intracellular uptake of MAb 5023 by breast carcinoma cells was also observed by fractionation of cells exposed to $^{125}$-I-labeled MAb (Table 1). $^{125}$I-MAb 5023 was internalized by the cells, and localized in the cytoplasm and in the nucleus (Table 1). None of the other MAb tested against gp120 was internalized by breast carcinoma cells.

Figure 2:
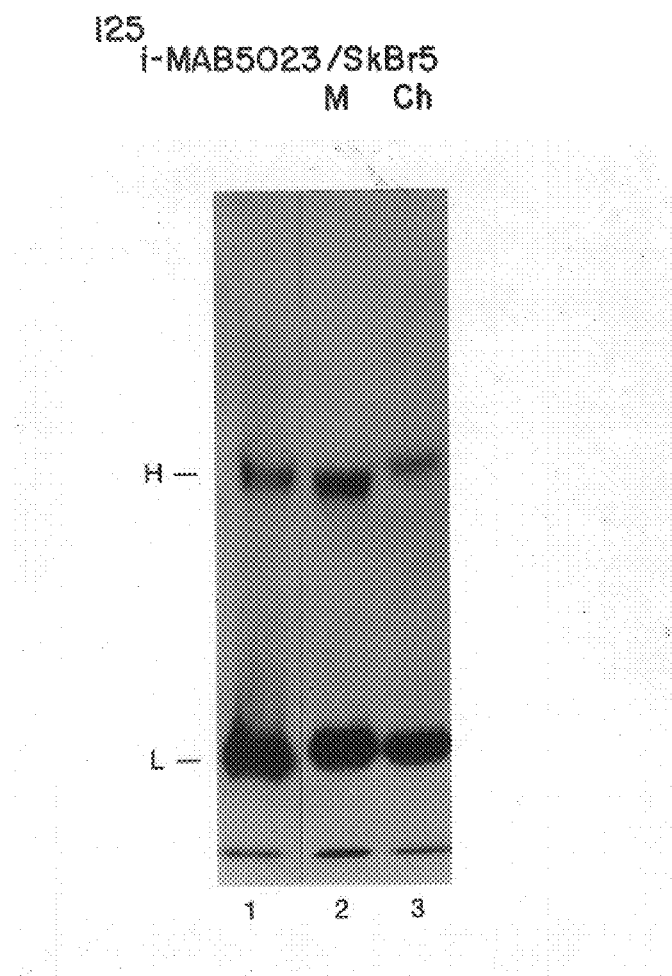
FIG. 2. Autoradiographic detection of free $^{125}$I-MAb 5023 (lane 1) and $^{125}$-I-MAb z5023 accumulated in the cytoplasm (lane 2) and in the chromatin (lane 3) after 24 h incubation with SKBr5 cells. Cytoplasm and chromatin were prepared from $5 \times 10^5$ cells.

Electrophoretic analysis of the internalized $^{125}$I-MAb 5023 indicated that after 24 h of incubation, $^{125}$I-MAb 5023 extracted from the cytoplasm and from the chromatin exhibited the same molecular weight of both heavy and light chains as did the native MAb (FIG. 2).

Identification of Breast Carcinoma Antigens Which Cross-React with the Internalizing MAb Against gp120

Figure 3A:
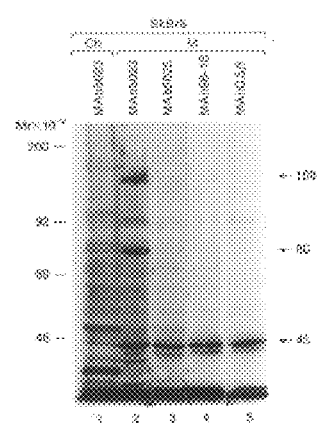
FIGS. 3A and 3B. Western blotting of different MAb against V3 loop of HIV-I gp120 with membrane (M) and chromatin (Ch) proteins of SkBr5 cells separated in a 7.5% (A) or 13% (B) polyacrylamide gel.
Figure 3B:
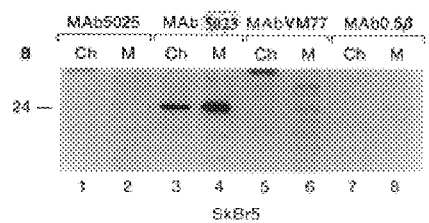

To determine whether internalization of MAb 5023 is mediated by a specific antigen, MAb 5023 and four other MAb were tested in Western blotting for reactivity with plasma membrane proteins and chromatin proteins of breast carcinoma SKBr5 (FIG. 3). High molecular weight proteins (200,000 $M_r$ and 45,000 $M_r$) were separated by electrophoresis in 7.5% polyacrylamide gel (FIG. 3A), and low molecular weight proteins by electrophoresis in 13% polyacrylamide gel (FIG. 3B). When the electrophoresis of proteins was performed in 7.5% polyacrylamide gel, the MAb 5023 reacted with a major 160,000 $M_r$ (p160) antigen of plasma membranes, a minor band of the $M_r$ 80,000 (p80), and a sharp band of the $M_r$, 45,000 (p45) (FIG. 3A, lane 2). Other MAbs against gp120 recognized p45, but not p160 and p80 (FIG. 3A, lanes 3–5). None of the protein bands detected in a plasma membrane fraction was detected in the chromatin (FIG. 3A, lane 1).

In a 13% polyacrylamide gel, a major protein-band of the $M_r$ 24,000 (p24) was detected in both the cell membrane fraction and in the chromatin by MAb 5023 (FIG. 3B, lanes 3 and 4). Other MAb tested did not recognize the p24 (FIG. 3B, lanes 1, 2, and 5–8).

Figure 4A:
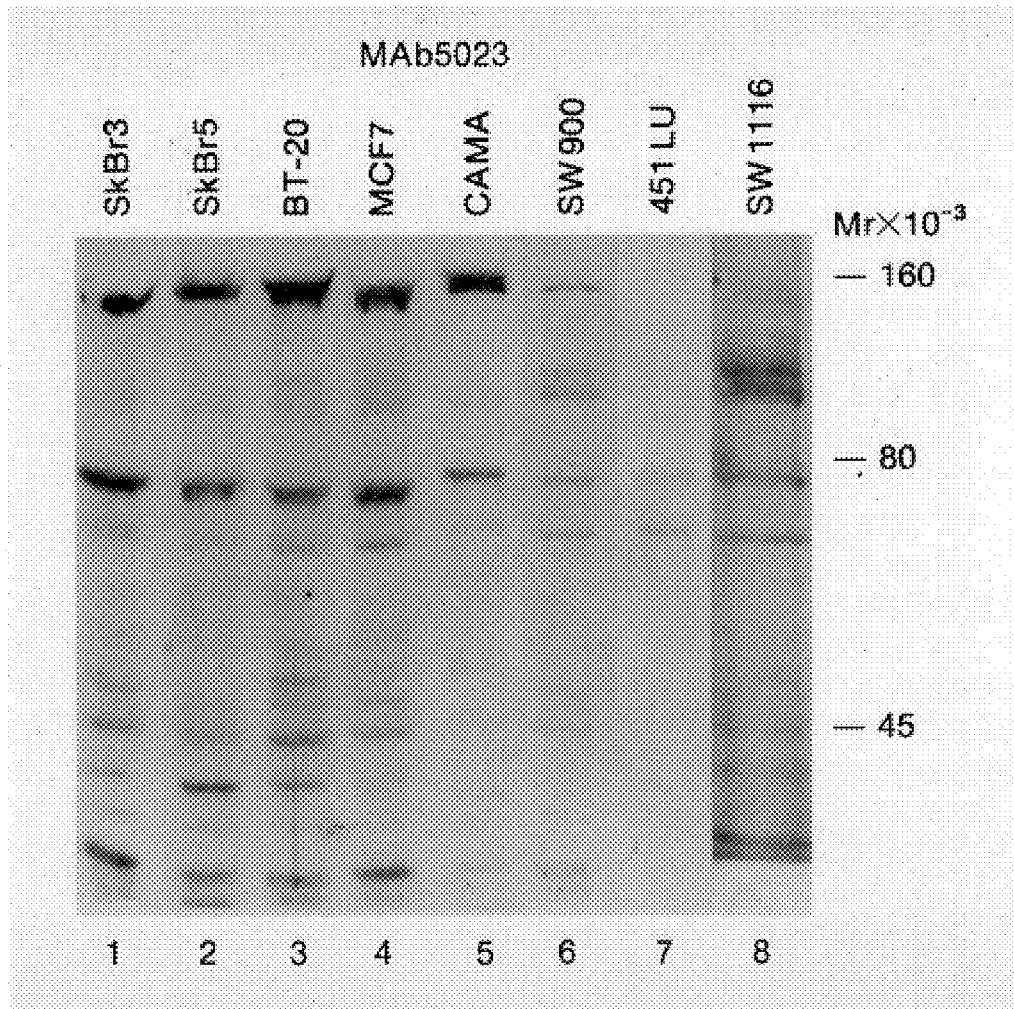
FIGS. 4A and 4B. Western blotting of MAb 5023 with membrane (M) and chromatin (Ch) proteins of different cell lines separated in 7.5% (A) or 13% (B) polyacrylamide gel.
Figure 4B:
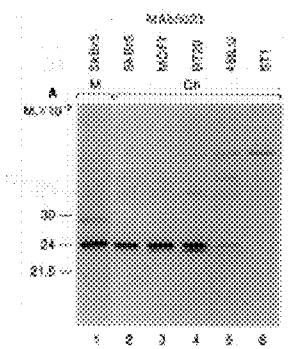

The test whether the breast carcinoma antigens which cross-react with MAb against gp120 of HIV-I are specific for the SKBr5 cell line, plasma membranes and chromatins from other breast carcinomas like SKBr3, MCF7, BT20, and CAMA were tested for reaction with MAb 5023 (FIG. 4). All breast carcinomas expressed the antigen p160, p80, and p45 in the membrane fraction (FIG. 4A), and p24 in both the membrane and the chromatin fractions (FIG. 4B). In the chromatin, in addition to the 24,000 $M_r$ protein, a 23,000 $M_r$ minor band was detected. Neither MAb 5023 (FIG. 4) nor any other MAb (not shown) recognized any of the plasma membrane antigens in colorectal carcinoma SW1116 (FIG. 4A, lane 8), lung carcinoma SW900 (FIG. 4A; lane 6), melanoma 451 Lu (FIG. 4A, lane 7), or T lymphocyte cell line ST1 (not shown). In melanoma cell line 451 Lu, but not in the other cell lines tested, a low expression of p24/p23 was detected in the chromatin (FIG. 4B, lane 5).

Figure 5:
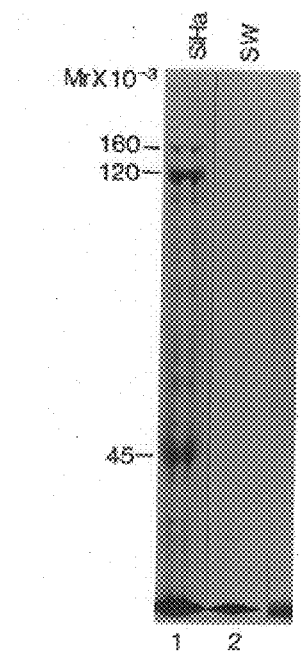
FIG. 5. Electrophoretic analysis (7.5% polyacrylamide gel) and autoradiographic detection of [$^{35}$S]methionine-labeled plasma membrane protein, immunoprecipitated by MAb 5023 from SKBr5 breast carcinoma cells (lane 1) and SW707 colorectal carcinoma cells (lane 2).

The typical profile of the Western reaction of MAb 5023 with the membrane protein was the same in the presence of the 1% 2-mercaptoethanol as in its absence. However, when the concentration of the 2-mercaptoethanol increased to 5%, p80 was present in higher concentrations than p160 (not shown). Immunoprecipitation of the plasma membrane fraction from [$^{35}$S]methionine-labeled SKBr5 cells with MAb 5023 revealed p160, p45 (FIG. 5, lane 1), and p24 (not shown). No proteins were immunoprecipitated by MAb 5023 from colorectal carcinoma SW707 cells (FIG. 5, lane 2), which confirms specificity of MAb 5023 reactivity with breast carcinoma antigens. The protein p80 detected by Western blotting in the plasma membrane fraction of breast carcinoma cells (FIG. 4A) was not detected in the immunoprecipitate. We suggest that p160 represents a dimeric form of p80, where the monomer p80 in the native form is not recognized by MAb 5023. We also cannot eliminate the possibility that p45 and p24 in the cell membrane represent degradation products of p160. Alternatively, all of the proteins recognized by MAb 5023 may originate from a one precursor protein. The relative amount of p160, p80, and p24 was similar in samples obtained from independent experiments. The relative amount of p45 varied from experiment to experiment.

Figure 6:
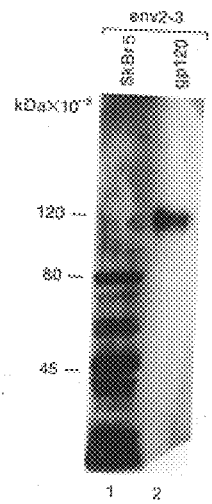
FIG. 6. Western blotting of human HIV-I-neutralizing antibodies to env-2-3 with SKBr5 breast carcinoma membrane proteins (lane 1) and HIV-I gp120 (lane 2). Proteins are separated in 7.5% polyacrylamide gel.

Breast Carcinoma Cell Cross-Reactivity and Internalization of Human HIV-I Neutralizing Sera HIV-I neutralizing human antibodies to env-2-3 (see Methods) reacted in Western blotting with 80,000 $M_r$ and 45,000 $M_r$ breast carcinoma cell membrane antigens (FIG. 6). It was likely, therefore, that a fraction of human antibodies to HIV-I recognized an epitope on breast carcinoma cells also recognized by MAb 5023. To determine whether human antibodies are internalized as the mouse MAb 5023 is, antibodies to env-2-3 were labeled with $^{125}$I and incubated with SKBr5 cells. A fraction of antibodies was found in the cytoplasm and in the nucleus (Table 1). The studies indicate that a fraction of human anti-HIV-I antibodies is able to penetrate breast carcinoma cells.

TABLE 1

Internalization of MAb 5023 against HIV-I gp120 and of human neutralizing antibodies after 24 h incubation with breast carcinoma cell line SKBr5

| MAb | Molecules per cell[a] | |
|---|---|---|
| | Cytoplasm | Nucleus[b] |
| 5023 | 1,890 | 5,450 |
| 5025 | 350 | 200 |
| VM77 | 60 | 20 |
| 0.5 | 35 | 60 |
| antibodies to env-2-3 | 2,456 | 10,080 |
| human IgG | 50 | 45 |

[a]Mean from four experiments; SD = 10% for MAb, 15% for antibody env-2-3 and 2% for human IgG which represents the control serum from HIV-I-negative people.
[b]Molecules bound to the chromatin, nucleoplasm, and nuclear membranes. Chromatin bound 85–95% of the nuclear $^{125}$I-MAb 5023.

Immunological Crossreactivity of Gynecological Cancer Antigens and HIV-I gp120

Figure 7A:
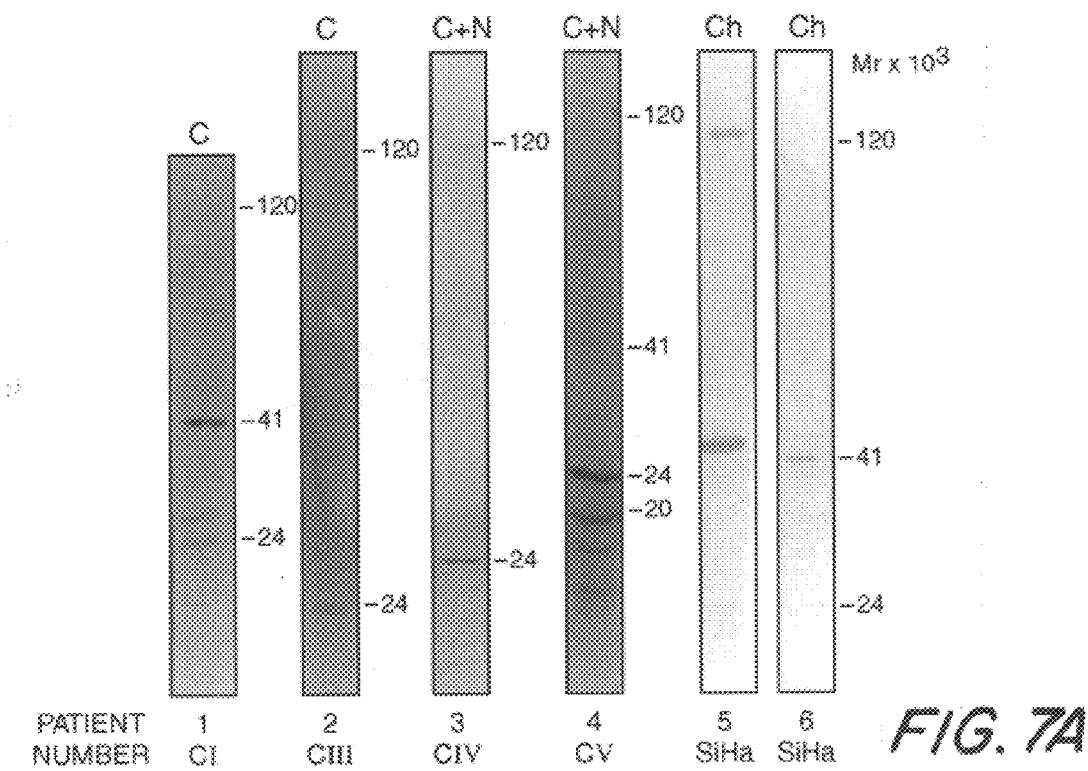
FIGS. 7A–7D. Western blotting of MAb 5023 (7A, 7B, 7C) and of MAb 5025 (7D) against HIV-I gp120 with plasmamembrane-containing cytoplasma (C) or nuclear fraction (N), or pure chromatin (Ch). Proteins were separated in 7.5–10% polyacrylamide gel. Different migration is due to the different time of electrophoresis and different gel concentrations. Prestained protein markers (high and low molecular weight from Bio-Rad) were used in each experiment.
Figure 7B:
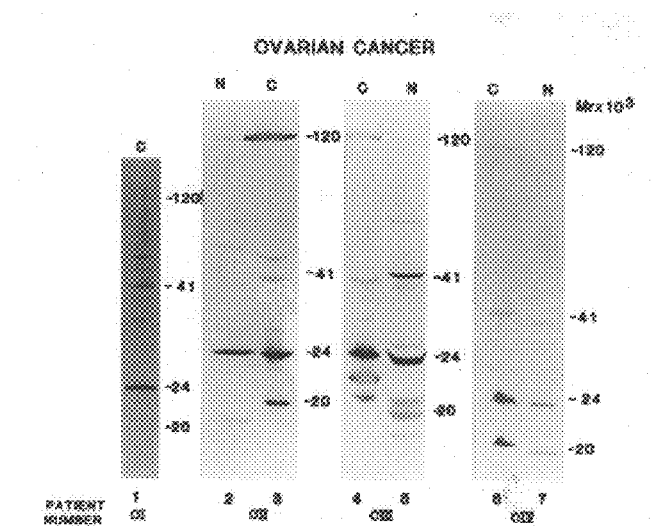
Figure 7C:
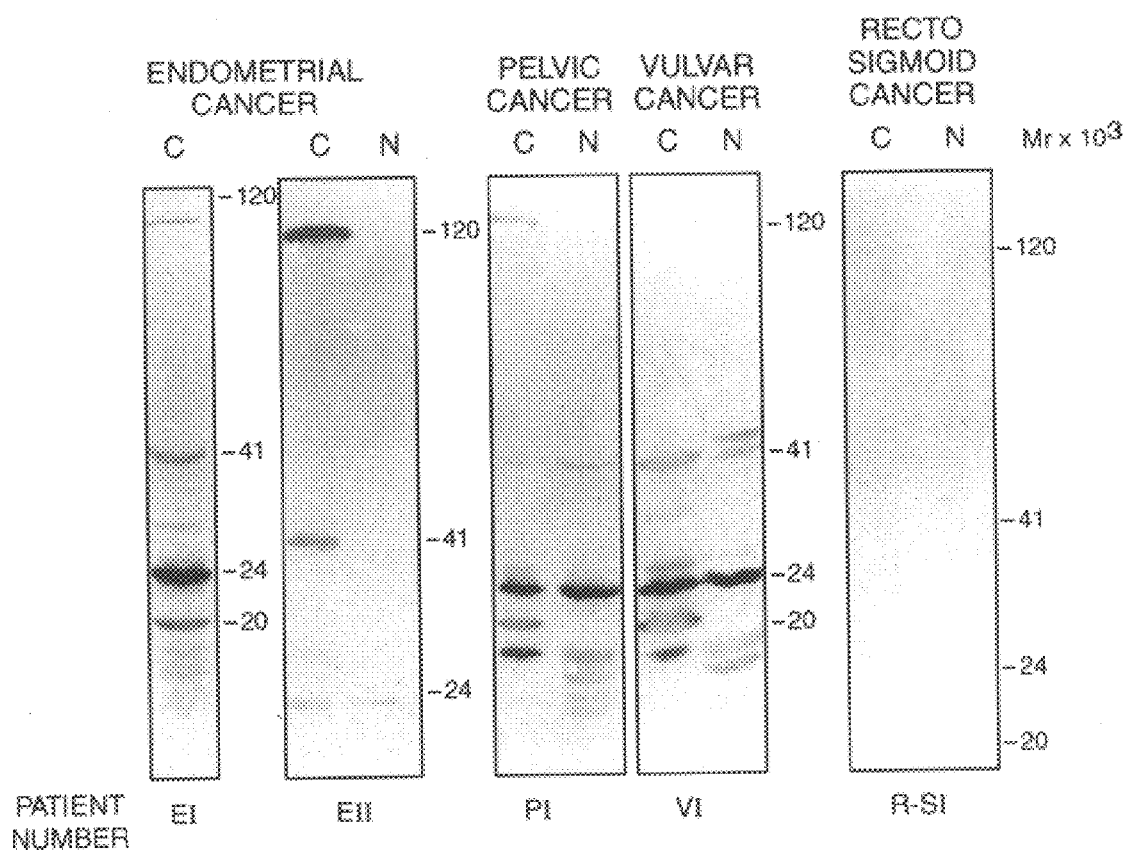
Figure 7D:
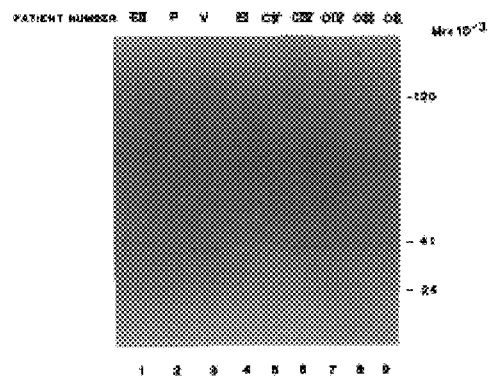

Gynecological cancer was obtained during standard surgical procedures performed in the Clinic of the Department of Obstetrics and Gynecology, University of Nebraska Medical Center. MAb 5023 detected antigen p120 in 5 of 6 tested ovarian cancer tissues, in 4 of 6 cervical cancer, endometrial cancer, vulvar cancer, and pelvic cancer of an unknown origin (FIG. 7). No proteins were specifically detected in rectal cancer. In addition to p120, protein p41 was detected in several cancers. Most of gynecological cancer tissues express also p24 in both cytoplasmic and nuclear fractions, while other proteins were detected only in the cytoplasm (FIG. 7A, B, C). Other MAb against HIV-I, like MAb 5025 did not detect any proteins.

Uptake of MAb 5023 By Isolated Nuclei $^{125}$I-MAb 5023, when incubated with nuclei isolated from SKBr5 breast carcinoma cells, was found to enter the nucleus and bind to the chromatin (Table 2). In control experiments, $^{125}$I-BSA was used instead of $^{125}$I-MAb. The $^{125}$I-BSA did not enter the nucleus. BSA ($M_r$ 65,000) is a much smaller molecule than immunoglobulin ($M_r$ 155,000), and therefore a passive diffusion of MAb due to nuclei damage during preparation or a nonspecific adsorption of immunoglobulins to the chromatin during nucleus fractionation may be eliminated. To determine whether MAb 5023 is taken up by the nucleus through the mediation of the N-acetylglucosamine-bound nuclear membrane receptor, which was found to mediate nuclear translocation of SV40 large T antigen and other proteins which contain the nuclear localization signal, the effect of WGA on nuclear uptake of MAb 5023 was tested. Nuclear translocation of MAb 5023 was significantly blocked by WGA (Table 2), which suggests that the nuclear membrane receptor may be involved in intranuclear translocation of this MAb.

Effect of MAb on RNA Synthesis and Cell Proliferation

RNA synthesis, measured as [3H]uridine incorporation into TCA-precipitable fraction, increased by 25% after 1 hr, and by 40% after 24 hr of cell exposure, compared to cells not exposed to MAb 5023 (Table 2).

TABLE 2

Effect of wheat germ agglutinin (WGA) on nuclear uptake of MAb 5023 in a cell-free system

| WGA concentration (mg/ml) | Nuclear membranes | MAb uptake[a] (cpm) Nucleoplasm | Chromatin |
|---|---|---|---|
| 0 | 11,700 | 1,530 | 100,000 |
| 0.625 | 10,400 | 950 | 87,000 |
| 1.25 | 9,950 | 860 | 75,800 |
| 2.5 | 5,840 | 610 | 42,900 |

[a]Five × $10^6$ nuclei/ml were incubated for 1 h at room temperature with $^{125}$I-MAb. Data are shown as mean from three experiments; SD = 5–8%.

Figure 8:
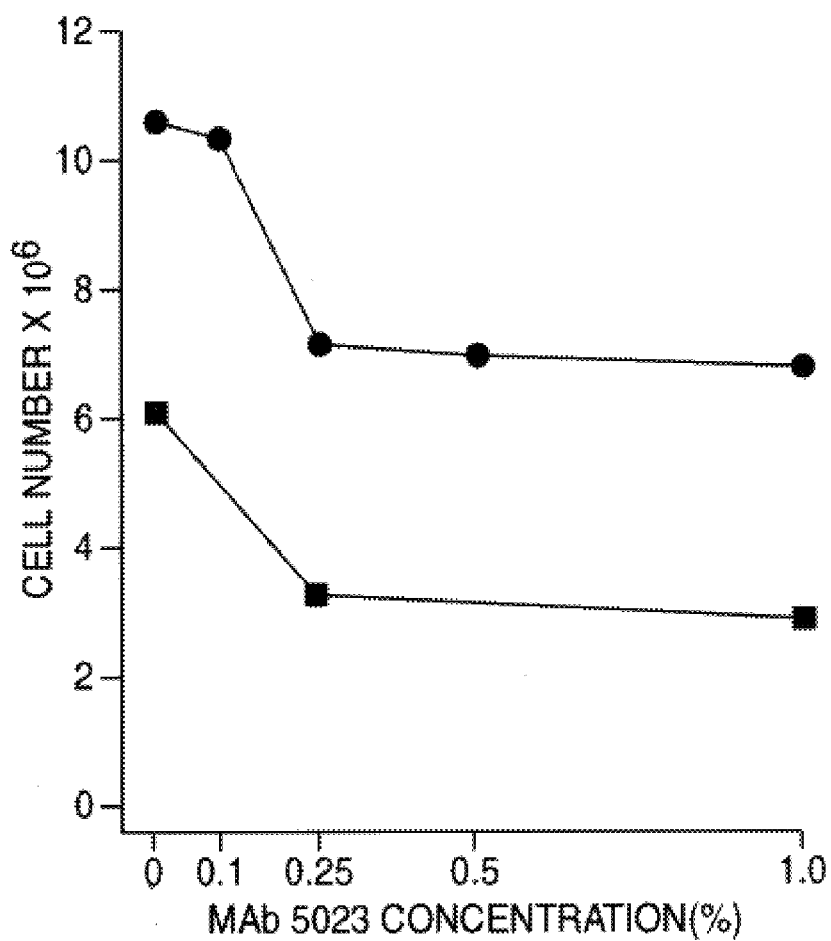
FIG. 8. Effect of MAb 5023 on growth of cervical cancer cell line SiHa. MAb was used as ascites, the concentration is given as ascites dilution in the medium 1%-concentration of ascites 1:100 which corresponds to approximate MAb concentration of 0.2 $\mu$g/ml. The inhibitory concentration 0.25 corresponds to 0.05 $\mu$g/ml.

MAb 5023, when added to the cell culture medium at the concentration 100 ng/ml, stimulated cell proliferation by 50% (Table 3). In contrast to the growth promoting action of MAb 5023 in breast cancer cells, growth of cervical cancer cell line SiHa which expresses a moderate level of p120 was by 30%–50% inhibited by MAb 5023 at the concentration 0.2 ug/ml (FIG. 8). It is likely that different structure of the cell surface antigen p160 and p120 may determine positive or negative growth-reaction to the MAb.

TABLE 3

Effect of MAb 5023 on RNA synthesis and cell proliferation

| MAb 5023 concentration (ng/ml) | Time of incubation | [38] uridine incorporation (cpm)[a] | Cell number (millions)[b] |
|---|---|---|---|
| 0 | 1 hr | 150,000 | |
| 100 | 1 hr | 188,000 | |
| 0 | 24 hr | 810,000 | |
| 100 | 24 hr | 1,250,000 | |
| 0 | 4 days | | 12.0 |
| 100 | 4 days | | 23.9 |

[a]Incorporation per constant number of cells, data are shown as mean from 2 experiments, SD = 10%
[b]Means from 4 experiments, SD = 10%

DISCUSSION

MAb developed against HIV-I gp120 were found to cross-react with antigens of breasts carcinoma cell lines and with antigens expressed in gynecological cancer. MAb 5023 developed against amino acid residues 308–322 of the variable V3 loop of HIV-I reacted in Western blotting with a 160,000 $M_r$ (P160) AND 80,000 $M_r$ (p80) cell surface antigens. Protein p160 seems to represent an oligomeric form of p80. In cervical, ovarian, endometrial and vulvar cancer MAb 5023 detects a 120,000 $M_r$ (p120) and a 41,000 $M_r$ (p41) proteins. Another MAb, 5025, directed against the same region 308–322, and MAb against amino acid regions 307–328 and 308–332, did not recognize p160 or p80. It was shown before that although MAb 5023 and MAb 5025 were developed against the same synthetic peptide, there are minor differences in the structure of the core epitope recognized by these MAb, which account for the several-fold higher affinity of MAb 5023 than that of MAb 5025. All of the MAb we tested recognized another cell membrane antigen, p45 in breast cancer and p41 in gynecological cancer. It is not established whether p45 and p41 represent independent proteins, a degradation, or processing products of p160 and p120 respectively. Since MAb 5023 was the only MAb which was able to enter breast carcinoma cells and translocate to the nucleus, it is likely that p160 (and p80) expresses a specific epitope which is critical for MAb internalization. An unspecific adsorption of the cell membrane-bound $^{125}$I-MAb 5023 to the chromatin during cell fractionation may be eliminated, since p160, p80, and p45 and p120 and p41 represent the specific markers of the cell membrane fraction and are not found in the chromatin. The fact that MAb 5023, but none of the other MAb, was internalized suggests that an antibody binding to a cell surface antigen is not sufficient to induce the process of internalization. Instead, a specific epitope of the cell surface antigen must be involved. The latest observation is consistent with our previous studies, which proved that only a few from many MAb developed against tumor-associated antigens are internalized, while others are unable to enter the cell.

MAb 5023, but non of the other MAb, recognized p24 in the cell membrane fraction and in the chromatin. In addition to the major band of p24, chromatin also expresses a minor p23 band. The chromatin did not show any tract of p160, p80, and p45, which eliminates the possibility that the cytoplasmic protein p24 attached unspecifically to the chromatin during cell fractionation. We suspect that p24 may be involved in binding the translocated MAb 5023 to the chromatin. It seems that p24 represents an antigen expressed on the cell surface, as well as in the chromatin of breast carcinoma cells and gynecological cancer cells. A weak expression of p24 was also observed in the chromatin of 451 in melanoma cells (FIG. 4B; lane 5). Chromatin of T lymphocytes did not express p24/p23. It is noteworthy that low expression of p24 was detectable in the plasma membrane fraction of several T lymphocyte cell lines. Binding of MAb 5023 to p24 was specifically inhibited by the synthetic peptide RIQRGPGRAFVTIGK (SEQ ID NO:1), towards which the MAb 5023 was developed.

Breast carcinoma antigens p160, p45 (FIG. 5), and p24 (not shown) were effectively immunoprecipitated by MAb 5023, which suggests that the native epitopes are also recognized by the MAb. Protein p80 was not immunoprecipitated, which suggest that the dimeric form (p160) expresses the epitope recognized by MAb 5023.

The results obtained show a definite immunological cross-reactivity of HIV-I gp120 and breast carcinoma and gynecological cancer antigens. Recently Khalife et al. reported an immunological cross-reactivity between the HIV-I virion infectivity factor (vif) and a 170 $M_r$ surface antigen of S. mansoni. However, there is no antigenic cross-reactivity between HIV-I structural proteins and S. mansoni antigens. Breast carcinoma antigen, p160 (and its monomeric form p80), deserves special attention, since it seems to contain an epitope whose recognition is critical for MAb internalization. The internalized MAb 5023 was developed against a short region of HIV-I gp120, covering amino acids 308–322

(RIQRGPGRAFVTIGK) (SEQ ID NO:1), but this MAb binds to the much shorter amino acid region GRAF (SEQ ID NO:9). It is likely that this core epitope must also be expressed in breast carcinoma p160. Alternatively, gp160 may express a conformation epitope homologous to that of HIV-I gp120. Whether the proteins of similar $M_r$ in breast carcinoma and HIV-I that cross-react with MAb against HIV-I gp120 represent products of human or retrovirus genes is currently unknown. We suspect that a retrovirus of strong homology to HIV-I may be present in breast carcinomas. Studies of breast carcinoma p160 and its immunological homology to gp120 focuses our attention on the possibility that antibodies able to penetrate the infected cells may be expressed during human HIV-infection. We have tested internalization of $^{125}I$ antibodies to env-2-3, which represent a fraction of the human HIV-I neutralizing antibodies able to recognize unglycosylated form of gp120. A fraction of antibodies to env-2-3 was internalized, and in Western blotting recognized p80 and p45 on the cell membrane (FIG. 6). The results suggest that internalized antibodies represent a fraction of antibodies synthesized by AIDS patients. Antibodies able to penetrate HIV-infected cells may play a critical role in inhibition of syncytia formation and in the process of virus neutralization.

Further studies conducted towards determining the origin of HIV-I crossreactive cancer antigens suggest that a Female Cancer Virus, with genetic and immunologic homology to HIV-I, is specifically expressed in breast and gynecological cancer.

Figure 9A:
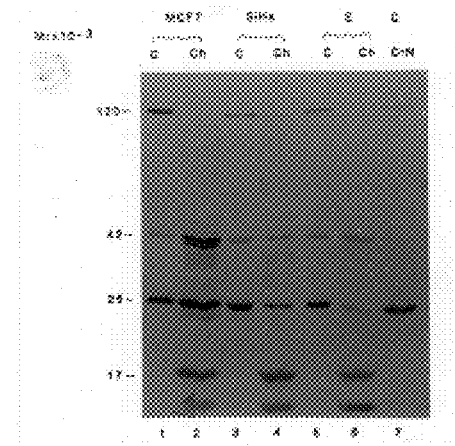
FIGS. 9A–9C. Electrophoretic analysis (10% gel) and Western blotting of cytoplasm (C) chromatin (Ch), or total C+N) proteins from cancer (A and B, lane 2) and normal cells (B, lane 2 and C) with MAb anti HIV-I gp120 (Cells or sections of cancer or normal tissues, obtained during standard surgical procedures, were homogenized in 0.35 M sucrose/10 mM KCl/1.5 mM $MgCl_2$/10 mM Tris-HCl (pH 7.6)/0.12% Triton X-100/12 mM 2-mercaptoethanol (1 ml/$3 \times 10^6$ cells or 0.25–1 ml/$cm^3$ tissue), and centrifuged at 600×g for 10 minutes. Supernatant was the crude, membrane-containing cycloplasmic fraction. The nuclear pellet was first washed with 0.2 M sucrose/3 mM $CaCl_2$/50 mM Tris-HCl (pH 7.6), and then with 0.14 M NaCl/10 mM Tris-HCl (pH 8.3) and centrifuged at 700×g for 10 minutes. The pellet was swollen in 1 mM Tris-HCl (pH 7.9) and centrifuged throughout the 1.7 M sucrose 10 mM Tris HCl (Ph 7) at 160,000×g for 80 minutes. Chromatin was pelleted at the bottom of the tube.
Figure 9B:
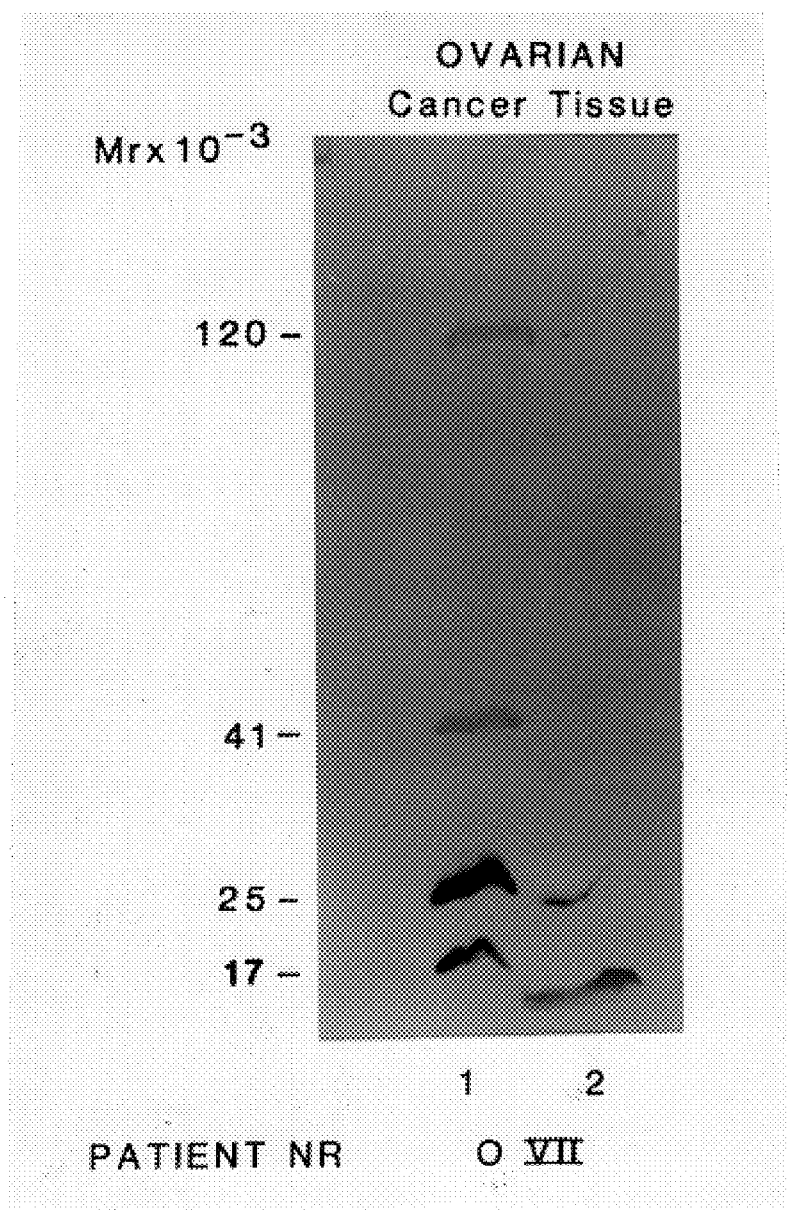
Figure 9C:
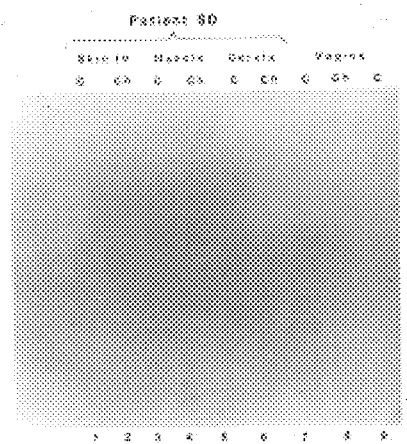

Western blot hybridizations, of cytoplasm and chromatin proteins from breast cancer MCF7 (FIG. 9A, lanes 1,2) and cervical cancer SiHa (FIG. 9A, lanes 3,4) cell lines, as well as from fresh endometrial (FIG. 9A, lands 5,6), cervical (FIG. 9A, lane 7) and ovarian (FIG. 9B) cancer, or mixed Mullerian tumor (FIG. 10, lanes 1,2) (DeBraekeleer M. et al., *Cancer Genet Cytogenet*, 59(2), 135–137, 1992.; Rakowicz-Szulczynska E. M., et al., in *Nuclear Localization of Growth Factors and of Monoclonal Antibodies*, ed. E. M. Rakowicz-Szulczynska, CRC Press, pp. 180–197, 1993) with MAb anti-HIV-I envelope protein gp120, revealed antigens p120, p42, p25 and p17 which correspond in size to the envelope proteins (p120, p42), major structural protein (p24) and myristylated Gag protein (p17) of HIV-I. Antigen p160, corresponding to the precursor of envelope proteins in HIV-I, was also detectable in smaller amounts in mixed Mullerian tumor (FIG. 10) as well as in several breast cancer cell lines (Rakowicz-Szulczynska E. M., et al., in *Nuclear Localization of Growth Factors and of Monoclonal Antibodies*, ed. E. M. Rakowicz-Szulczynska, CRC Press, pp. 180–197, 1993; Rakowicz-Szulczynska E. M., et al., *Breast Cancer Res Treatment*, 1994) and gynecological cancer (Rakowicz-Szulczynska E. M. et al., *Breast Cancer Res Treatment*, 1994; Rakowicz-Szulczynska E. M., et al., *Breast Cancer Res Treatment*, 1994). Antigens p160 and p120 were selectively detected in the cytoplasmic fraction, while proteins p42 and p25 were detected in both cytoplasmic and chromatin fractions (FIG. 9 & 10). Normal ovarian tissue (FIG. 9B), skin, muscles, normal cervical tissue and normal vaginal mucosa tested negative (FIG. 9C), which indicates that MAb anti-HIV-I reacted selectively with cancer. Melanoma, lung carcinoma and colorectal carcinoma also did not react with MAb anti-HIV-I gp120 (Rakowicz-Szulczynska E. M., et al., in *Nuclear Localization of Growth Factors and of Monoclonal Antibodies*, ed. E. M., Rakowicz-Szulczynska, CRC Press, pp. 180–197, 1993; Rakowicz-Szulczynska E. M., et al., *Breast Cancer Res Treatment*, 1994), which proves that HIV-crossreactive antigens are selectively associated with breast and gynecological cancer.

MAb, which recognized p160, p120, p42 and p24 in cancer cells, was developed against amino acid sequences 308–322 (RIQRGPGRAFVTIGK) SEQ ID NO:1 of the variable loop of HIV-I gp120, and this MAb binds to the epitope GRAF (SEQ ID NO:9) (Durda P. J., Bacheler L., Clapham P., Jenowski A. M., Leece B., Matthews T. J., McKnoght A., Pomerantz R., Rayner M. & Weinhold K. J. *AIDS Res Human Retroviruses*, 6, 1115–1118, 1988; Langedijk J. P. M., Back N. K. T., Durda P. J., Goudsmit J. & Meloen R. E. *J. Gen Virol*, 72, 2519–2526, 1991). G Preceding RAF is critical for cancer antigen binding, since another MAb, which recognizes RAF but forms weak interactions with G, does not recognize cancer antigens (Rakowicz-Szulczynska E., et al., *Antibody Immunoconj Radiopharm*, 6, 209–219, 1993). To assess the specificity of MAb anti-HIV-I gp120 binding to the cancer cell epitopes, Western blots were performed in the presence and absence of the peptide RIQRGPGRAFVTIGK SEQ ID NO:1 towards which the MAb was developed. Cytoplasm, isolated from mixed Mullerian tumor, was electrophoretically separated in 10% polyacrylamide gel with SDS, blotted into the PVDF membrane and exposed to anti-HIV-I gp120 MAb which was preincubated (FIG. 10B) or not preincubated (FIG. 10A) with the peptide. Antigens p120, p42 and p25 strongly reacted with MAb anti-HIV-I gp120 which was not preincubated (FIG. 10A), but did not react with MAb which was preincubated with the peptide (FIG. 10B). Thus, the peptide RIQRGPGRAFVTIGK SEQ ID NO:1 competitively blocked binding of the MAb to the cancer antigens (FIG. 10B, lanes 1,2) indicating in HIV-I gp120, that at least the epitope GRAF (SEQ ID NO:9), which is recognized by the MAb, must also be present in cancer antigens. The heterogeneity of cancer antigens recognized by MAb anti-HIV-I gp120 remains unclear since only gp120 and its precursor p160 were recognized by the same MAb in the extract obtained from HIV-I infected cells (FIG. 10C). Since the peptide blocked binding of MAb anti-HIV-I gp120 to all cancer antigens (p160, p120, p42 and p25) nonspecific interactions may be excluded.

To determine whether any extended genetic homology between HIV-I genome and cancer antigens can be anticipated, polymerase chain reaction (PCR) was performed with DNA from cancer cells using HIV-I-derived primers. Two sets of primers were derived from HIV sequences located in different regions than those encoding the variable region recognized by MAb anti-HIV-I gp120. The first set of primers (SK 68/SK 69):

SK 68 (7801–7820, region gp41 Env):5'-AGCAGCAGGAAG-CACTATGG-3' SEQ ID NO:2

SK 69 (7922–7942, region gp41 Env):5'-CCAGACTGTGAGTTG-CAACAG-3' SEQ ID NO:3 consisted of two 20-mers derived from the gene for envelope protein gp41 of HIV-I (Laure P., Courgnaud V., Rouzioux C., Blanche S., Veber F., Burgard M., Jacomet C., Griscelli C. & Brechot C. *Lancet*, 2, 538, 1988). The second set of primers (P1/P2):

P1 (764–786, region Gag):5'-TACATCAGGCCATATCACCTAC-3' SEQ ID NO:4

P2 (1041–1056, region Gag):5'-TGAAGGTACTAGTACTTC-CTGC-3' SEQ ID NO:5 was derived from the Gag gene of HIV-I (Ou C. Y., Kwok S., Mitchell S. W., Mack D. H., Sninsky J. J., Krebs J. W., Feorino P., Warfield D. & Schochetman G. *Science*, 239, 295, 1988). Both sets of HIV-derived primers initiated the PCR in the presence of DNA isolated either from HIV-I infected lymphocytes, or from breast cancer MCF7, cervical cancer SiHa cells, endometrial cancer or mixed Mullerian tumor obtained during surgery (FIG. 11). Negative reaction was obtained with control DNA isolated from normal skin (FIG. 11). PCR with DNA isolated from noninfected lymphocytes is reportedly negative (Laure F., et al., *Lancet,* 2, 538, 1988) and was also negative in our studies (not shown).

The PCR products obtained with primers SK 68/SK 69 were of the same size (approximately 140 bp) in the case of MCF7, SiHa and gynecological cancer DNA, as in the case of the DNA isolated from HIV-infected cells which was used as the template (FIG. 11A). The sequential analysis of the amplified fragments, revealed 140 bp of cancer DNA with no significant homology to any known human gene. Of the 140 bp, 105 bp were identical in at least two of three cancers tested and 53 bp were identical in all three cancers (FIG. 12). 21 bp located at the 3' end of the amplified region of MCF7 breast cancer DNA were identical to the HIV sequences (FIG. 12). In SiHa cell DNA, 20 of 21 bp were identical to HIV sequences. In endometrial cancer DNA, 19 bp were identical to HIV-I sequences, 2 bp were different and 2 bp were inserted within the region of homology with HIV-I, MCF7 and SiHa.

The DNA fragments amplified by PCR in the presence of the second set of primers (P1/P2-Gag derived) was only 130 bp-long in breast, cervical and endometrial cancer DNA, comparing to the 304 bp-long fragment obtained with DNA isolated from HIV-I infected cells (FIG. 11B) and showed a limited homology with HIV-I genomer (not shown).

Amplification of breast, cervical, endometrial and mixed Mullerian tumor DNA sequences, in the presence of HIV-I gp41- and Gag-derived primers, high homology of cancer and HIV-I sequences, in addition to the immunological homology of cancer antigens with the variable loop of HIV-I gp120, strongly suggested that retroviral sequences homologous to HIV-I genome might be integrated with breast and gynecological cancer DNA. Presence of HIV in cell cultures or in the fresh cancer tissue was eliminated since HIV-I p24 was tested negative. Since the DNA fragments, amplified in the presence of HIV-I Gag-derived sequences, were shorter in cancer DNA than in HIV-I integrated DNA, HIV infection of human cancer cells may be completely eliminated. The fact that similar DNA sequences were amplified in the presence of DNA isolated from SiHa and MCF7 cell lines, as in the presence of DNA isolated from endometrial cancer obtained during the surgery, ruled out contamination of cell cultures with a virus associated with several human cell cultures (Ilyin K. V., Bykovsky A. P. & Zhdanov V. M. *CA,* 32, 89–96, 1973) Porovic M., Kalyanaraman V. S., Reitz M. S. & Sarngadharan M. G. *Am J Cancer,* 30, 93–99, 1982). To verify the existence of a female cancer associated virus related to HIV-I, selectron microscopic studies were performed with SiHa and MCF7 cells.

Figure 13A:
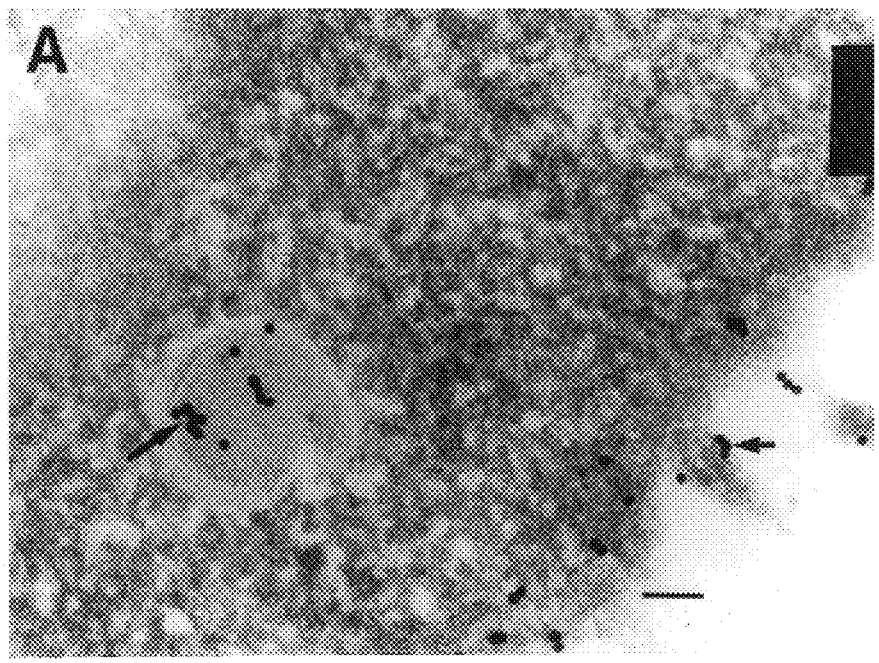
Figure 13B:
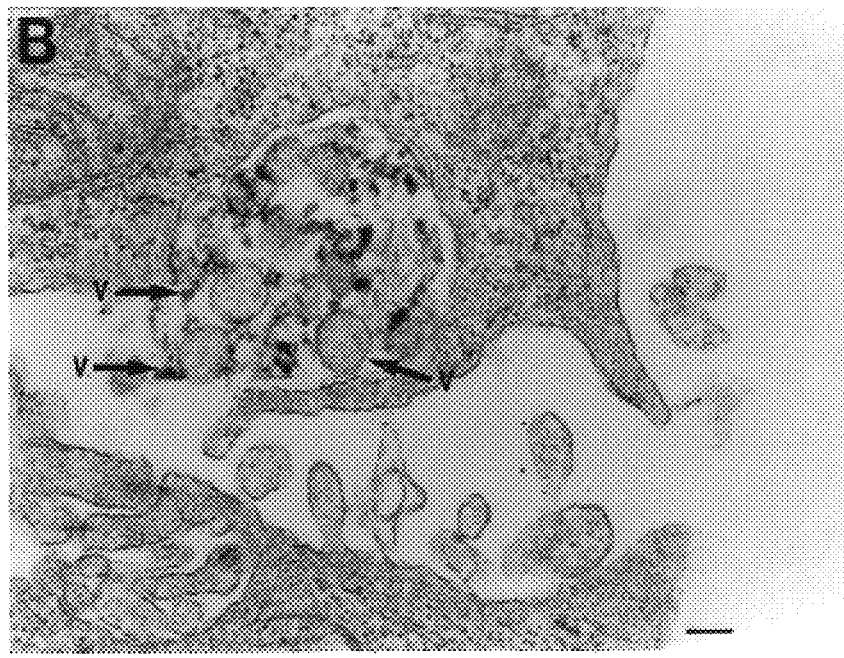
Figure 13C:
Figure 13D:
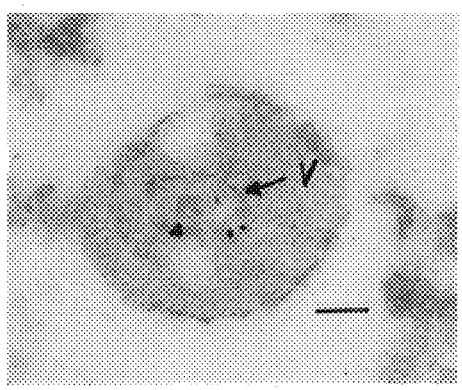
Figure 13E:
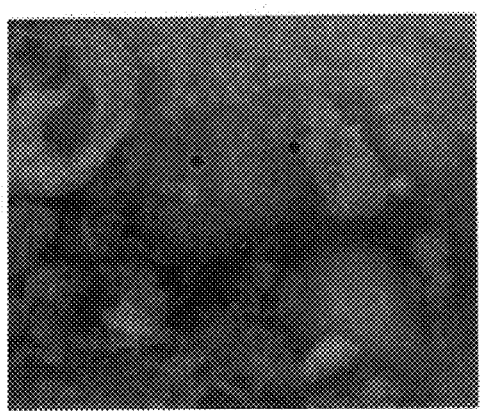
Figure 13F:
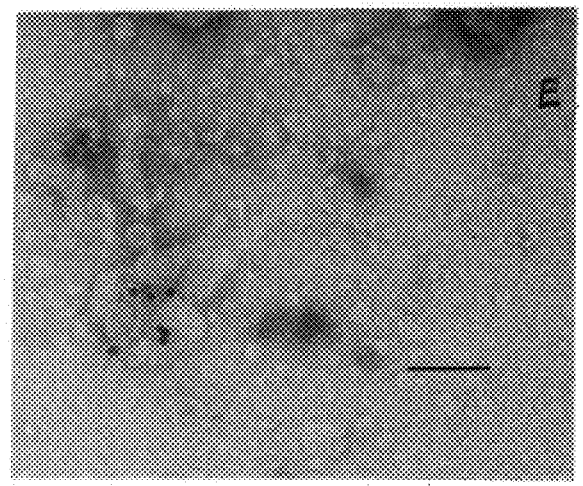
Figure 13G:
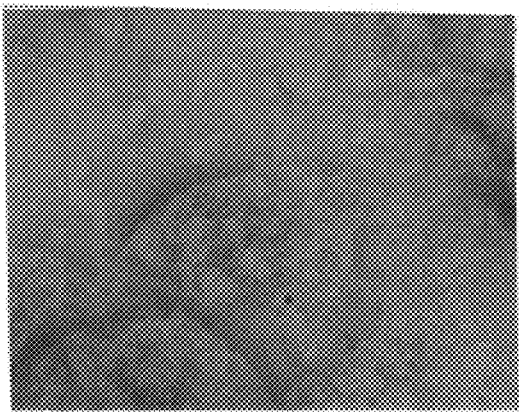

Electron microscopic analysis of the thin sections of SiHa cervical cancer and MCF7 breast cancer cells revealed large, membrane-coated vesicles (vacuoles) located in the cytoplasm (FIG. 13A), as well as on the edge of cells (FIG. 13B) and outside the cells (FIG. 13C). Immuno-gold staining with MAb anti-HIV-I gp120 visualized the same large vesicles localized in the cytoplasm (FIG. 13A,B). Strong immunogold labeling of the villi-like structures on the cell surface, as well as intracellular and extracellular particles, was also observed (FIG. 13B). Visualization of a cross-section (FIG. 13D) of the large cytoplasmic vesicle, located close to the cell surface, revealed several oval-shaped, viral-like particles localized within the vesicle. The viral-like particles were also "budding" from the extracellular vacuoles (FIG. 13B). The size of the particles was approximately 120–150 nm. Immuno-gold staining of the membrane-coated vesicles, obtained by ultracentrifugation (100,000 g×1 hr) of the SiHa or MCF7 cell culture medium, revealed similar viral-like particles localized inside the membrane covered vesicles (FIG. 13E). Negative staining of purified viral particles is shown in FIG. 13E. The size, 120 nm, of the virus might be suggested. Immuno-gold labeling of the isolated viral particles with MAb anti-gp120 strongly supports the hypothesis about the viral origin of HIV-crossreactive cancer antigens and is consistent with genetic homology observed on the DNA level. Analysis of the localization of the virus-like particles strongly suggests that the virus is either synthesized inside the membrane-coated vesicles or, after synthesis, buds into the intracytoplasmic vacuoles, which are then secreted to the cell surface, fuse with the membrane and release viral particles through exocytosis. Exocytosis of the virus-containing vesicles might be responsible for the formation of the characteristic "peninsula-like" surface of the cancer cells, with very long villi-like structures. Alternatively, intact vesicles might be removed from the cells and the viral particles would, thus, be budding from the surface. In contrast to HIV and several other viruses, which usually bud from the cell surface (Levy J. A. *The Retroviridae,* Plenum Press, vol 1, 2 & 3), cancer associated viral particles were never found to be budding directly from the cell surface.

An identical, spherical shape suggested that these particles might represent a virus of the D type. D retrovirus is associated with Simian AIDS and was first isolated in 1970 from a naturally occurring breast carcinoma in a captive rhesus macaque (Chopra H. C. & Mason M. M. *Cancer Res,* 30, 2081–2086, 1970). Several laboratories demonstrated D-type virus in established human cell lines (Ilyin K. V., Bykovsky A. F. & Zhdanov V. M., *CA,* 32, 89–96, 1973; Porovic M. Kalyanaraman V. S., Reitz M. S. & Sarngadharan M. G. *Am. J. Cancer,* 30, 93–99, 1982), however, origin of these viruses was never established. Immuno-gold labeling of the viral particles detected in cervical cancer SiHa and breast cancer MCF7 cells with MAb anti HIV-I gp120, confirms the above described genetic and immunological homology of the identified virus with HIV. Since PCR analysis revealed homologous sequences and Western blot analysis revealed identical proteins in cervical, breast and endometrial cancer cell lines or mixed Mullerian tumors isolated from the patients, we suggest that the retrovirus is of human origin. Human origin and cancer association of the HIV-like proteins gp120, gp42 and p25 is strongly supported by the fact that identical proteins were found in most ovarian, cervical, mixed Mullerian and vulvar cancers obtained during surgery, as well as in five different breast carcinoma cell lines (Rakowicz-Szulczynska E. M., Kaczmarski W., Steimer K. S. & Durda P. J. Internalized antibodies as a potential tool against retroviral disease, in *Nuclear Localization of Growth Factors and of Monoclonal Antibodies,* ed. E. M. Rakowicz-Szulczynska, CRC Press, pp. 180–197, 1993; Rakowicz-Szulczynska E., Raso V., Kaczmarski W. & Durda P. J. *Antibody Immunoconj Radiopharm,* 6, 209–219, 1993; Rakowicz-Szulczynska E. M., McIntosh D. G. & Smith M. L. *Infect Dis Obstet Gynecol,* 1994, in press; Rakowicz-Szulczynska E. M., McIntosh D. G. & Smith M. L. Mechanisms of cancer growth promotion by HIV-I neutralizing antibodies, submitted to *Breast Cancer Res Treatment,* 1994).

Labeling of breast cancer cells with MAb anti-HIV-I gp120 was also observed when using immunofluorescence technique (Rakowicz-Szulczynska E. M., Kaczmarski W., Steimer K. S. & Durda P. J. Internalized antibodies as a potential tool against retroviral disease, in *Nuclear Localization of Growth Factors and of Monoclonal Antibodies,* ed. E. M. Rakowicz-Szulczynska, CRC Press, pp. 180–197, 1993). Fluorsceine staining of the cytoplasm and of the nucleus was very strong, which confirmed the observation that MAb anti-HIV-I gp120 is recognized and internalized as well by breast cancer cells as by HIV-I infected T-lymphocytes (Rakowicz-Szulczynska E., Raso V., Kaczmarski W. & Durda P. J. *Antibody Immunoconj Radiopharm,* 6, 209–219, 1993).

To evaluate whether the identified HIV-crossreactive cancer antigens play a role in malignant growth of cells, antisense oligonucleotides, complementary to the identified sequences of cancer DNA, have been synthesized and used to treat SiHa and MCF7 cells in vitro (FIG. 14). Antisense oligonucleotides RAK-I (21-mer 5'-CCAGACTGTGAGTTGCAACAG-3') SEQ ID NO:6, RAK-II (15-mer 5'-CAACAGCCTACAACC-3') SEQ ID NO:7 and RAK-III (15-mer 5'-TCTTCTAATCCCAAA-3') SEQ ID NO:8, complementary to the cancer DNA sequences amplified with HIV-I derived primers, inhibited growth of cells by 50, 70 and 30%, respectively, within 4 days (FIG. 14). Control antisense oligonucleotides (5'-TGTGACATCAGGCTCAAATC-3') SEQ ID NO:14 did not inhibit cell growth. The results indicate that expression of the HIV-associated cancer antigens is critical for growth of breast and cervical cancer cells. Since the antisense oligonucleotides inhibited activity of reverse transcriptase in cell culture by 95%, it may be suggested that the identified retrovirus plays a significant role in female cancer growth promotion.

The cancer virus seems to contain a hybrid genome with homology to different isolates of HIV, since the MAb anti-HIV-I gp120 was developed against the gp120 variable domain of HIV-I$_{IIIb}$, and PCR primers SK 68/SK 69 originated from the isolate HIV-I$_{ARV-2}$. The 21 bp segment of breast, cervical and endometrial cancer DNA, identical to HIV sequences, is highly conserved in different strains of HIV-I. The sequences preceding the conserved segment were, to a certain degree, homologous to several HIV-I strains.

The HIV-like antigens p120, p42 and 25 were detected selectively in breast and gynecological cancer, but not in normal tissues and, therefore, represent unique markers of female malignancies. One of the HIV-crossreactive antigens is detectable in the blood of breast cancer patients and it seems to represent the novel marker of spontaneous female malignancies. Since antisense oligonucleotide RAK-I, II and III inhibited growth of breast and cervical cancer cells in vitro, the novel Female Cancer Virus represent a promising target for cancer diagnosis, prognosis and therapy.

From the foregoing it will be appreciated that, although specific embodiments of the invention have been described herein for the purposes of exemplification, various modifications may be made without deviating from the spirit and scope of the invention. Accordingly, the invention is not to be limited except as set forth in the appended claims.

What is claimed is:

1. A method for detecting breast carcinoma-associated antigens in a biological sample comprising:

contacting the biological sample, suspected of containing the breast carcinoma-associated antigens, with monoclonal antibody 5023 which recognizes HIV-I crossreactive cancer antigens; and detecting the presence of immunocomplexes formed between said antibody and said breast carcinoma-associated antigens, wherein said HIV-I crossreactive cancer antigens cannot be detected in a healthy biological sample; and wherein the method includes a control to ensure that the biological sample does not contain HIV-antigen.

2. A method for detecting HIV-I crossreactive gynecological cancer-associated antigens in a biological sample comprising:

contacting the biological sample, suspected of containing the HIV-I crossreactive gynecological cancer-associated antigens, with monoclonal antibody 5023 which recognizes HIV-I crossreactive cancer antigens, and detecting the presence of immunocomplexes formed between said antibody and said HIV-I crossreactive gynecological cancer-associated antigens, wherein said HIV-I crossreactive cancer antigens cannot be detected in a healthy biological sample; and wherein the method includes a control to ensure that the biological sample does not contain HIV-I antigens.

3. The method of claim 1 or 2 wherein said antibody is labeled.

4. The method of claim 3 wherein said label is selected from the group consisting of enzymes, immunogold, fluorochromes, radioisotopes, and luminescers.

5. The method of claim 1 or 2 wherein the step of detection is by enzyme reaction, fluorescence, luminescence emission, or radioactivity.

6. The method of claim 1 or 2 wherein the biological sample is selected from the group consisting of bodily secretions, bodily fluids, and tissue specimens.

7. The method of claim 1 or 2 wherein the biological sample is separated by gel electrophoresis prior to exposing to said antibody.

8. The method of claim 1 or 2 wherein said antibody reacts with an epitope having the protein sequence GRAF (SEQ. ID No. 9).

9. The method of claim 1 or 2 wherein the immunocomplexes are immobilized.

10. The method of claim 9 wherein the immunocomplexes are immobolized onto substrates selected from the group consisting of glass, synthetic polymers, synthetic resins, cellulose, nitrocellulose, and metals.

* * * * *